(12) United States Patent
Nadjar et al.

(10) Patent No.: US 7,953,230 B2
(45) Date of Patent: May 31, 2011

(54) METHOD AND SYSTEM FOR PHYSIOLOGICAL SIGNAL PROCESSING

(75) Inventors: Hamid Sheikhzadeh Nadjar, Waterloo (CA); Robert L. Brennan, Kitchener (CA); Julie Johnson, Waterdown (CA); Etienne Cornu, Cambridge (CA)

(73) Assignee: On Semiconductor Trading Ltd., Hamilton (BM)

( * ) Notice: Subject to any disclaimer, the term of this patent is extended or adjusted under 35 U.S.C. 154(b) by 1388 days.

(21) Appl. No.: 11/174,366

(22) Filed: Jul. 1, 2005

(65) Prior Publication Data

US 2006/0056641 A1 Mar. 16, 2006

(30) Foreign Application Priority Data

Sep. 15, 2004 (CA) .................................... 2481631

(51) Int. Cl.
*A61B 7/04* (2006.01)
(52) U.S. Cl. ........................ 381/67; 600/528; 600/586
(58) Field of Classification Search .................... 381/67, 381/98, 56, 122, 102; 600/481, 483, 508, 600/528, 586
See application file for complete search history.

(56) References Cited

U.S. PATENT DOCUMENTS

| | | | |
|---|---|---|---|
| 4,263,919 A | 4/1981 | Levin | |
| 4,478,224 A | 10/1984 | Bailey | |
| 4,686,998 A | 8/1987 | Robbins | |
| 4,898,179 A * | 2/1990 | Sirota | 600/483 |
| 5,209,237 A | 5/1993 | Rosenthal | |
| 5,213,108 A * | 5/1993 | Bredesen et al. | 600/528 |
| 5,243,992 A | 9/1993 | Eckerle et al. | |
| 5,243,993 A | 9/1993 | Alexander et al. | |
| 5,301,679 A * | 4/1994 | Taylor | 600/586 |
| 5,347,583 A * | 9/1994 | Dieken et al. | 381/67 |
| 5,365,934 A | 11/1994 | Leon et al. | |
| 5,492,129 A | 2/1996 | Greenberger | |
| 5,524,631 A | 6/1996 | Zahorian et al. | |
| 5,596,993 A | 1/1997 | Oriol et al. | |
| 5,610,987 A | 3/1997 | Harley | |

(Continued)

FOREIGN PATENT DOCUMENTS

CA 2 481 629 A1 3/2006

(Continued)

OTHER PUBLICATIONS

R.E. Crochiere, et al., "Performance Limitations of a New Subband Adaptive System for Noise and Echo Reduction," *Multirate Digital Signal Processing*, Prentice-Hall Signal Processing Series, Prentice-Hall, pp. 325-326, at least as early as Jun. 30, 2005.

(Continued)

*Primary Examiner* — Vivian Chin
*Assistant Examiner* — Jason R Kurr
(74) *Attorney, Agent, or Firm* — Pearne & Gordon LLP

(57) ABSTRACT

A method and system for processing of physiological signals is provided. The system processes information signals in subband-domain associated with the physiological signals in time-domain. The information signals are obtained by one or more over-sampled filterbanks. The method and system possibly synthesizes the subband signals obtained by subband processing. The method and system may implement the analysis, subband processing, and synthesis algorithms on over-sampled filterbanks, which are implemented on ultra low-power, small size, and low-cost platform in real-time. The method and system may use over-sampled, Weighted-Overlap Add (WOLA) filterbanks.

37 Claims, 19 Drawing Sheets

U.S. PATENT DOCUMENTS

| | | | |
|---|---|---|---|
| 5,662,105 | A | 9/1997 | Tien |
| 5,666,959 | A | 9/1997 | Deans et al. |
| 5,685,317 | A * | 11/1997 | Sjostrom ................ 600/528 |
| 5,737,433 | A | 4/1998 | Gardner |
| 5,738,104 | A | 4/1998 | Lo et al. |
| 5,908,393 | A | 6/1999 | Albrecht et al. |
| 6,002,777 | A * | 12/1999 | Grasfield et al. ............ 381/67 |
| 6,236,731 | B1 | 5/2001 | Brennan et al. |
| 6,240,192 | B1 | 5/2001 | Brennan et al. |
| 6,245,025 | B1 | 6/2001 | Torok et al. |
| 6,262,943 | B1 | 7/2001 | Clarke |
| 6,551,251 | B2 | 4/2003 | Zuckerwar et al. |
| 6,575,915 | B2 | 6/2003 | Nissila et al. |
| 6,650,917 | B2 | 11/2003 | Diab et al. |
| 6,662,043 | B1 | 12/2003 | Shine |
| 6,768,979 | B1 * | 7/2004 | Menendez-Pidal et al. .. 704/226 |
| 7,110,554 | B2 | 9/2006 | Brennan et al. |
| 7,416,531 | B2 * | 8/2008 | Mohler .................... 600/528 |
| 7,458,939 | B2 * | 12/2008 | Munk ..................... 600/528 |
| 2003/0063759 | A1 | 4/2003 | Brennan et al. |
| 2004/0071284 | A1 | 4/2004 | Abutalebi et al. |

FOREIGN PATENT DOCUMENTS

| | | |
|---|---|---|
| JP | 2002301066 | 10/2002 |
| WO | 98/47313 A2 | 10/1998 |

OTHER PUBLICATIONS

Julie Johnson et al., "An Ultra-Low Power Subband-Based Electronic Stethoscope", ICASSP 2006, IEEE, I-4244-0469-X/06, pp. III-1156 to III-1159, 2006.

Afonso V.X. et al., "Multirate Processing of the ECG using Filter Banks", Computers in Cardiology, 1996, Sep. 8-11, 1996, pp. 245-248.

Afonso V.X. et al., "Filter Bank-Based Processing of the Stress ECG", in Proc. 17th Annual Int. Cont. of the IEEE/EMBS, vol. 2, Sep. 20-23, 1995, pp. 887-888.

Afonso V.X. et al., "Comparing Stress ECG Enhancement Algorithms", in IEEE Engineering in Medicine and Biology, May/Jun. 1996, pp. 37-44.

Afonso V.X. et al., "Filter Bank-Based ECG Beat Classification", in Proc. 19th Annual Int. Conf. of the IEEE/Embs, Oct. 30 - Nov. 2, 1997, pp. 97-100.

Afonso V.X. et al., "ECG Beat Detection Using Filter Banks", IEEE Trans. on Biomedical Eng., vol. 46, No. 2, Feb. 1999, pp. 192-202.

AASE S.O., "Filter bank design for subband compression of ECG signals", at least as early as Jun. 30, 2005, 6 pages.

Aydin M.C. et al., "ECG Data Compression by Sub-Band Coding", IEEE Electronics Letters, vol. 27, Issue: 14, No. 4, Feb. 14, 1991, pp. 359-360.

Brennan R. and Schneider T., "A Flexible Filterbank Structure for Extensive Signal Manipulations in Digital Hearing Aids", Proc. IEEE Int. Symp. Circuits and Systems, 1998, pp. 569-572.

Hermann D. et al., "Low-Power Implementation of the Bluetooth Subband Audio Codec", IEEE, in Proc. of the 2004 ICASSP, May 17-21, 2004, 4 pages.

AASE S.O., "Filter Bank Design for Subband ECG Compression", in Proc. 18th Annual Int. Conf. of the IEEE/EMBS, 1996, pp. 1382-1383.

* cited by examiner

FIGURE 10  Subband WOLA-based FX-LMS with reference microphone, with analog ANC

Figure 12: Stethoscope

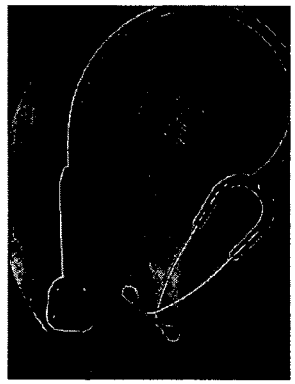
Figure 16: Top view of stethoscope prototype
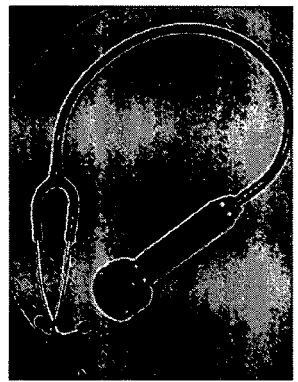
Figure 17: Bottom view of stethoscope prototype
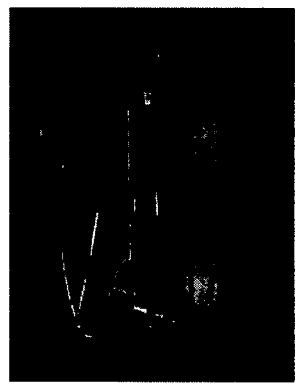
Figure 18: Side view of stethoscope prototype

METHOD AND SYSTEM FOR PHYSIOLOGICAL SIGNAL PROCESSING

FIELD OF INVENTION

This invention relates to signal processing, more specifically to processing of input signals including physiological signals.

BACKGROUND OF THE INVENTION

The use of digital signal processing for physiological signals has been an active long-term field of research. Various digital signal processing (DSP) techniques have been applied to physiological signal sources such as heartbeat, ECG/EKG, EMG, heart and lung sounds, and many others. In almost all cases however, the employed methods need considerable computation power leading to moderate to high levels of power consumption. Many portable devices have been built, but often they are not as miniaturized as they ideally could be.

As early as 1981, U.S. Pat. No. 4,263,919 reveals methods and systems of analog signal processing for heartbeat detection and artifact discrimination using ECG signals. U.S. Pat. No. 4,478,224 discloses a heartbeat rate measuring system for monitoring a patient's EKG signal with artifact rejection. It combines analog signal processing (ASP) with DSP on a microprocessor to estimate the heartbeat rate using a time-domain method. Similarly, U.S. Pat. No. 4,686,998 combines both ASP and DSP to measure the temperature and heartbeat remotely on a hand held battery-powered device.

U.S. Pat. No. 5,209,237 discloses detecting noisy physiological signals (like fetal heartbeat) using multiple sensors, and a combination of ASP and DSP noise cancellation techniques such as correlation cancellation and Wiener filtering.

As the use of DSP techniques in signal processing becomes more dominant, several inventions report implementations of more complicated DSP methods. These include U.S. Pat. Nos. 5,596,993, 5,666,959 and 6,245,025 B1 all pertaining to fetal heartbeat monitoring, and U.S. Pat. Nos. 5,908,393, and 6,262,943 B1 both discussing the reduction of noise in biological signals. More elaborate and recent multi-channel DSP techniques are disclosed in U.S. Pat. Nos. 6,551,251 B2, 6,662,043 B1, and 6,575,915 B2.

Adaptive noise cancellation (ANC) techniques have been extensively used to process physiological signals. U.S. Pat. Nos. 5,492,129 and 5,662,105 disclose the use of ANC methods for noise reduction in stethoscopes and physiological signals. In U.S. Pat. No. 6,650,917 B2, the use of various variants of ANC method for physiological signal processing (particularly for blood oxiometery measurements) is disclosed.

Active noise control is also suggested for signal processing in stethoscopes and similar devices in U.S. Pat. Nos. 5,610,987 and 5,737,433.

U.S. Pat. Nos. 5,243,992, 5,243,993, 5,365,934, 5,524,631, and 5,738,104 disclose heartbeat rate detection through the use of autocorrelation function estimation. It is notable that they all estimate the autocorrelation function in the time-domain.

Filterbanks have also been proposed for use in physiological signal processing (PSP). In a series of research papers from 1995 to 1999, Afonso et al. have disclosed the use of perfect reconstruction filterbanks to process the ECG signal (V. X Afonso et al., "Multirate processing of the ECG using filter banks", Computers in Cardiology 1996, 8-11 Sep. 1996, pp. 245-248; V. X Afonso et al., "Filter bank-based of the stress ECG", in Proc. 17th Annual Int. Conf. of the IEEE/EMBS, pp. 887-888 vol. 2, 20-23 Sep. 1995; V. X Afonso et al., "Comparing stress ECG enhancement algorithms", in IEEE Eng. In Medicine and Biology, pp. 37-44, May/June 1996; V. X Afonso et al., "Filter bank-based ECG beat classification", in Proc. 19th Annual Int. Conf. of the IEEE/EMBS, Oct. 30-Nov. 2, 1997; V. X Afonso et al., "ECG beat detection using filter banks", IEEE Trans. on Biomedical Eng., Vol. 46, No. 2, pp. 192-202, February 1999). Other researchers have used similar methods as reported for example in S. O. Aase, "Filter bank design for subband ECG compression", in Proc. 17th Annual Int. Conf. of the IEEE/EMBS, pp. 1382-1383, 1996; M. C. Aydin et al., "ECG data compression by sub-band coding", IEEE Electronic Letters, Vol. 27, Issue: 14, pp. 359-360, 14 Feb. 1991.

However, current methods for processing physiological signals described above have inherent limitations when deployed in standalone instruments. For example, there is a long delay between the time when the signal occurs and when the processing completes. The conventional methods are not well suited for deployment on parallel systems. The conventional methods are not well suited for deployment on cost effective fixed-point (16 bit) systems. Although some conventional methods process in the frequency-domain, they do not allow independent subband processing. The conventional instruments are too big or heavy, and the power consumption is too high, limiting the portability of the systems. The output (including audio) quality is not sufficient. Feature extraction is not sufficiently robust. Due to low-power and small-size constraints, more efficient and complicated signal processing methods cannot be deployed.

It is therefore desirable to provide a new method and system, which can efficiently process signals including possible physiological signals, and can implement physiological signal processing on ultra low-power, small size and low-cost platform in real-time.

SUMMARY OF THE INVENTION

It is an object of the invention to provide a novel method and system that obviates or mitigates at least one of the disadvantages of existing systems.

The method and system processes information signals in subband-domain associated with input signals in time-domain. The information signals are obtained by one or more over-sampled filterbanks. The method and system possibly synthesizes the subband signals obtained by subband processing. The method and system may implement the analysis, subband processing, and synthesis algorithms on over-sampled filterbanks, which are implemented on an ultra low-power, small size, and low-cost platform in real-time. The method and system may use over-sampled, Weighted-Overlap Add (WOLA) filterbanks.

According to an aspect of the invention, there is provided a method of processing one or more input signals including one or more physiological signals, which includes the steps of: providing one or more information signals in a frequency-domain, the information signals being obtained by converting one or more input signals in a time-domain through one or more over-sampled analysis filterbanks; implementing subband signal processing on the information signals in accordance with an application associated with the physiological signal; and combining the results of the subband signal processing to provide one or more output signals.

According to a further aspect of the present invention there is provided a system for processing one or more input signals including one or more physiological signals, which includes of: module for providing one or more information signals in a frequency-domain, the information signals being obtained by converting one or more input signals in a time-domain through one or more over-sampled analysis filterbanks; module for implementing subband signal processing on the information signals in accordance with an application associated with the physiological signal; and module for combining the results of the subband signal processing to provide one or more output signals.

According to a further aspect of the present invention there is provided a stethoscope for processing a physiological sound signal, which includes: a diaphragm for amplifying the physiological sound signal; a microphone for transforming the physiological sound signal to an electrical signal; one or more programmable digital signal processors for processing one or more electrical signals, implementing one or more over-sampled, WOLA filterbanks; a resonation chamber enclosing the microphone; and a receiver for making the output of the programmable digital signal processor audible.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 16 is a diagram showing a top view of the prototype of the stethoscope of FIG. 12;

FIG. 17 is a diagram showing a bottom view of the prototype of the stethoscope of FIG. 12;

FIG. 18 is a diagram showing a side view of the prototype of the stethoscope of FIG. 12.

DETAILED DESCRIPTION OF THE PREFERRED EMBODIMENTS

Figure 1:
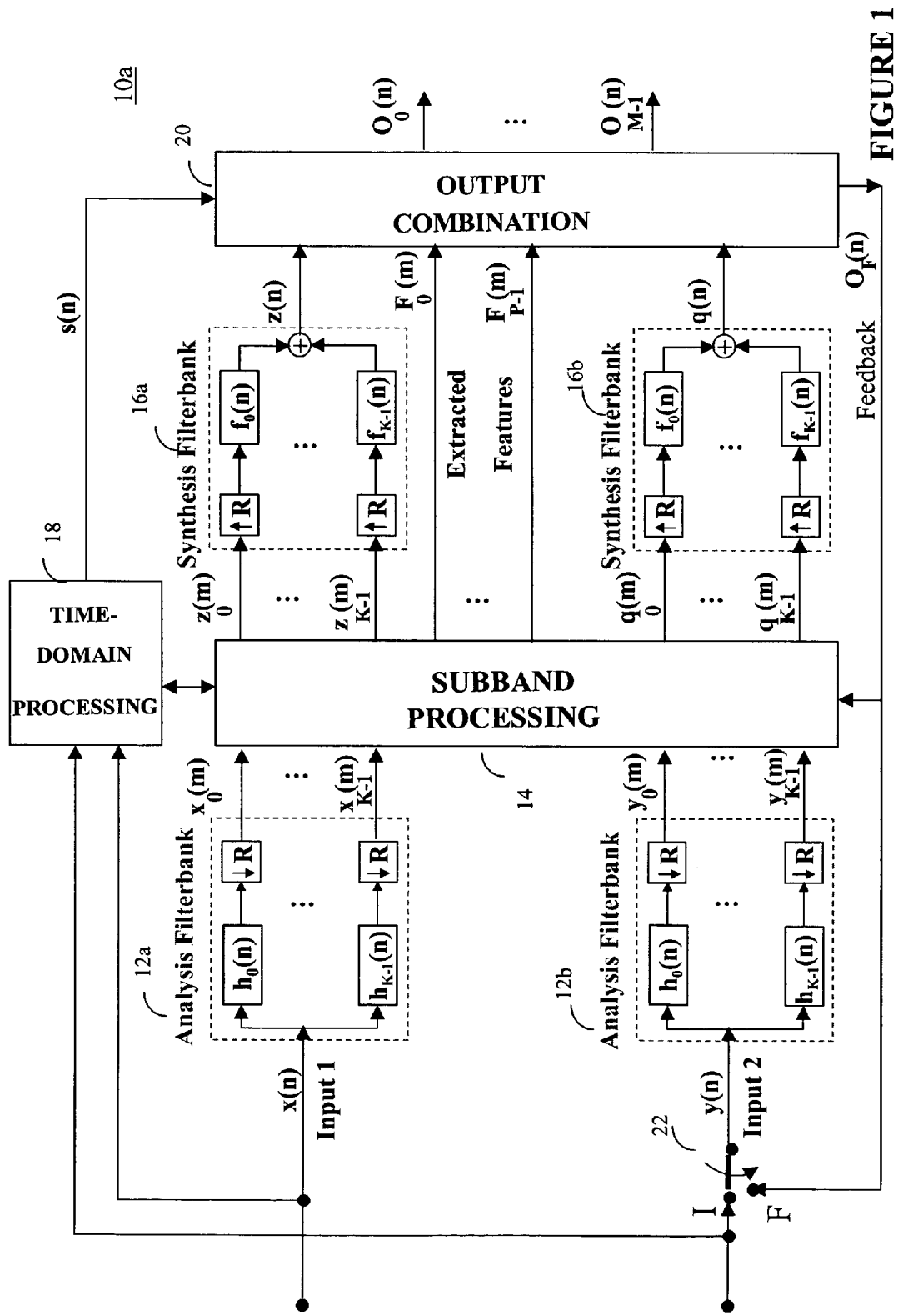
FIG. 1 is a diagram showing a physiological signal processing system in accordance with an embodiment of the present invention.

FIG. 1 shows a physiological signal processing system $10a$ in accordance with a first embodiment (a) of the present invention. One or more input (possibly physiological) signals are converted from the time-domain into the frequency-domain by an over-sampled analysis filterbank ($12a$, $12b$), generating subband information signal sets ($x_i(m)$, $y_i(m)$, i=0, 1, . . . , K−1) that undergo subband processing at subband processing block 14. In FIG. 1, two input signals x(n), y(n) are shown as examples. However, more than two inputs may be provided to the system $10a$. The processed signals ($z_i(m)$, $q_i(m)$, i=0, 1, . . . , K−1) are then converted from the frequency-domain into the time-domain by an over-sampled synthesis filterbank ($16a$, $16b$). As a result, one or two time-domain output signals z(n), q(n) are obtained. In FIG. 1, two output signals z(n), q(n) are shown. However, more than two time-domain output signals may be obtained.

It is noted that in the description, the terms "block" and "module" may be used interchangeably. It is noted that in the description, "input signal" or "information signal" may be possibly physiological signals including heart beats (including fetal heart beats), lung sounds, bowel/gastrointestinal sounds, ECG/EKG signals.

Each output signal (z(n), q(n)) represents the results of the subband processing 14 on one or more input signals. Thus joint or individual processing of the inputs are both possible. Examples are adaptive (joint) processing of two or more inputs, or single-input noise reduction of each input individually. Features ($F_l(m)$, l=0, 1, . . . , P−1) may be extracted in the frequency domain from any of the input signals. An example of a feature is the heartbeat rate for heartbeat input signals. Parallel to the subband processing 14, time-domain processing 18 of the input signals may take place. The time-domain processing 18 may interact with the subband processing block 14 in different ways. The subband processing 14 may control or be controlled by the time-domain processing 18. For example, signal energy might be measured in time-domain with low-delay to control the subband processing 14. As another example, the subband processing 14 may find an optimal adaptive filter in frequency-domain, and convert the adaptive filter back into the time-domain for application to the signals in the time-domain processing block 18 with low latency. Finally correlation processing may be done in time-domain processing block 18 independent of the subband processing 14. Generally, any form of time-domain processing is possible.

The output (s(n)) of the time-domain processing 18 may be combined with other time-domain outputs (z(n), q(n)) in an output combiner 20 to obtain one or more final outputs ($O_i(n)$, i=0, 1, . . . , M). The output combiner 20, for example, can obtain linear combinations of the outputs (z(n), q(n), s(n), $F_l(m)$, l=0, 1, . . . , P−1) or perform more sophisticated signal processing on the outputs. The output combiner 20 can also provide one or more feedback signals (such as $O_F(n)$ of FIG. 1) for controlling the subband processing block 14 or as its input, or to be used as input signals. For example, at input y(n)

in FIG. 1, a switch 22 is on "F" position for the feedback signal to play the role of an input signal, and on "I" position to route input signal y(n) to the system 10a.

Figure 2:
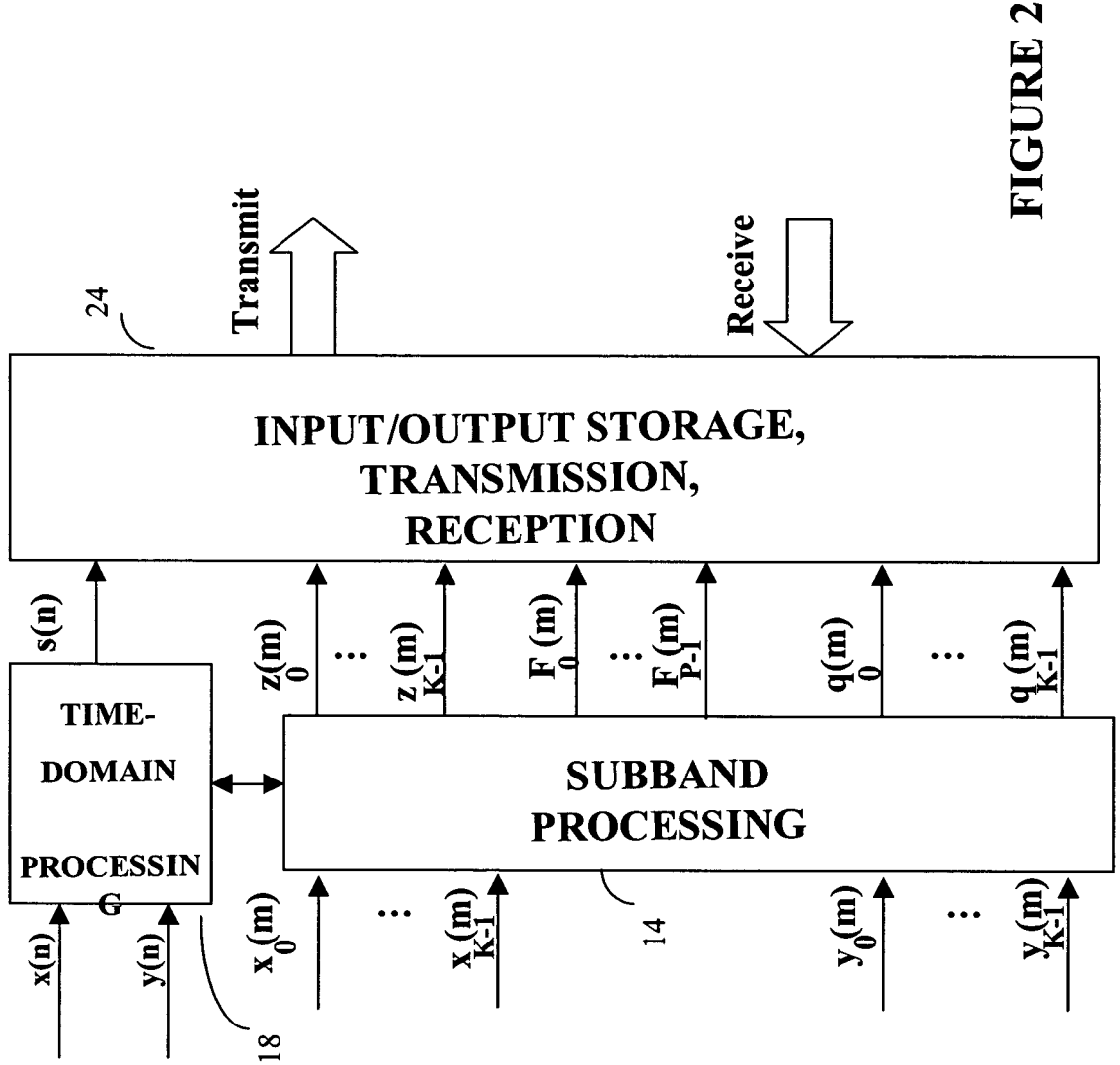
FIG. 2 is a diagram showing an example of the input/output stage, transmission and reception applied to the system of FIG. 1.

In the processing stage (14, 18) of FIG. 1, all or some of the input/output signals (x(n), y(n), $x_i$(m), $y_i$(m), $z_i$(m), $q_i$(m), i=0, 1, ..., K−1, $F_l$(m), l=0, 1, ..., P−1, s(n)) may be stored for future use, or transmitted to other systems, possibly after proper compression or encoding. The processing block (14, 18) can also retrieve the previously stored signals mentioned above or may receive them from other systems. If the signals are already compressed or encoded in any way, the system will decompress or decode them prior to usage. For clarity, this feature is not shown in FIG. 1 and is rather shown separately in FIG. 2. FIG. 2 shows an input/output storage, transmission, and reception block 24. Block 24 is capable of storing all or some of the input/output signals of the subband processing, the time-domain processing or a combination thereof, transmitting them to other systems, and receiving them from other systems. The feature of FIG. 2 is applicable to the physiological signal processing systems 10b-10i of FIGS. 3-10.

Figure 3:
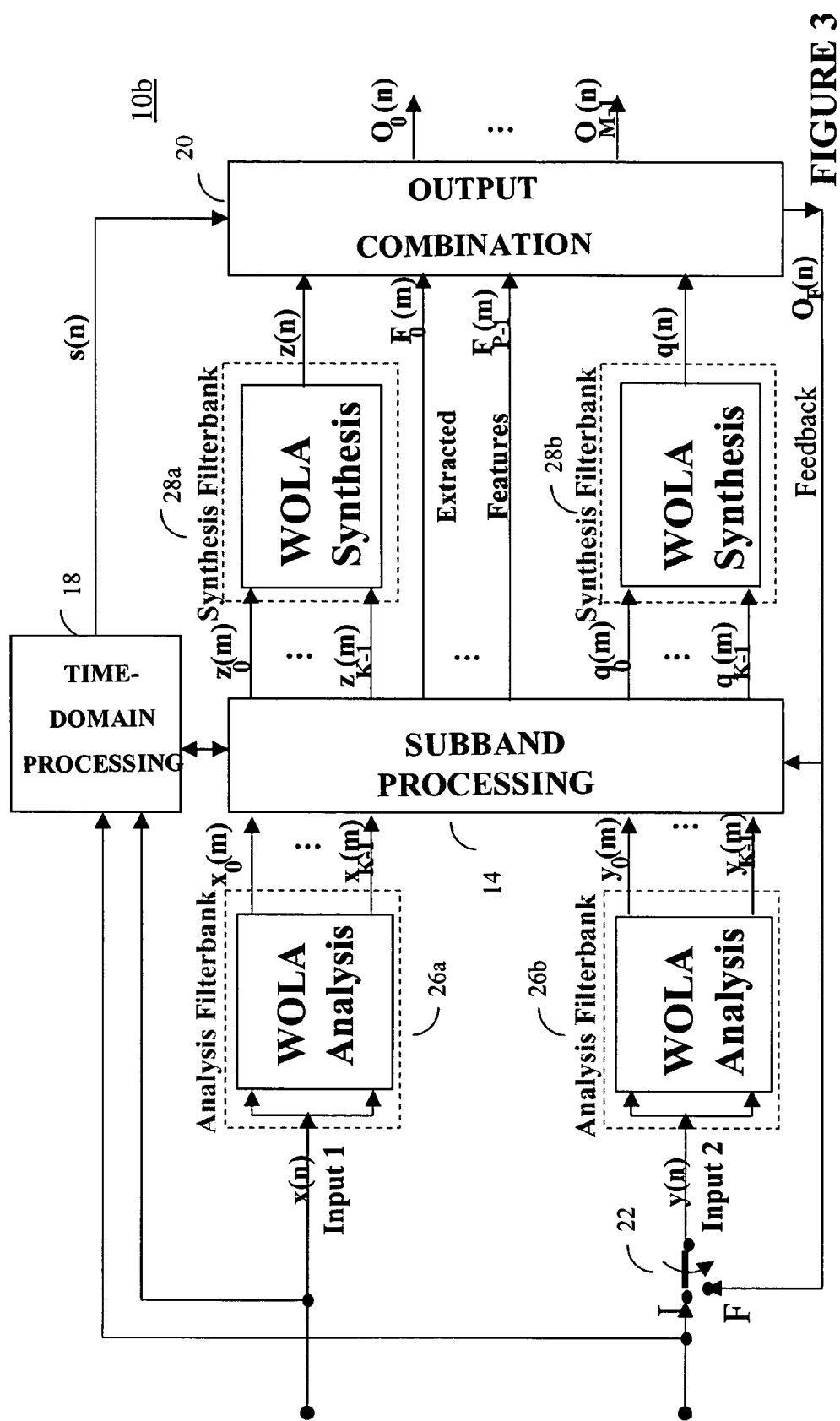
FIG. 3 is a diagram showing a physiological signal processing system in accordance with a further embodiment of the present invention.
Figure 4:
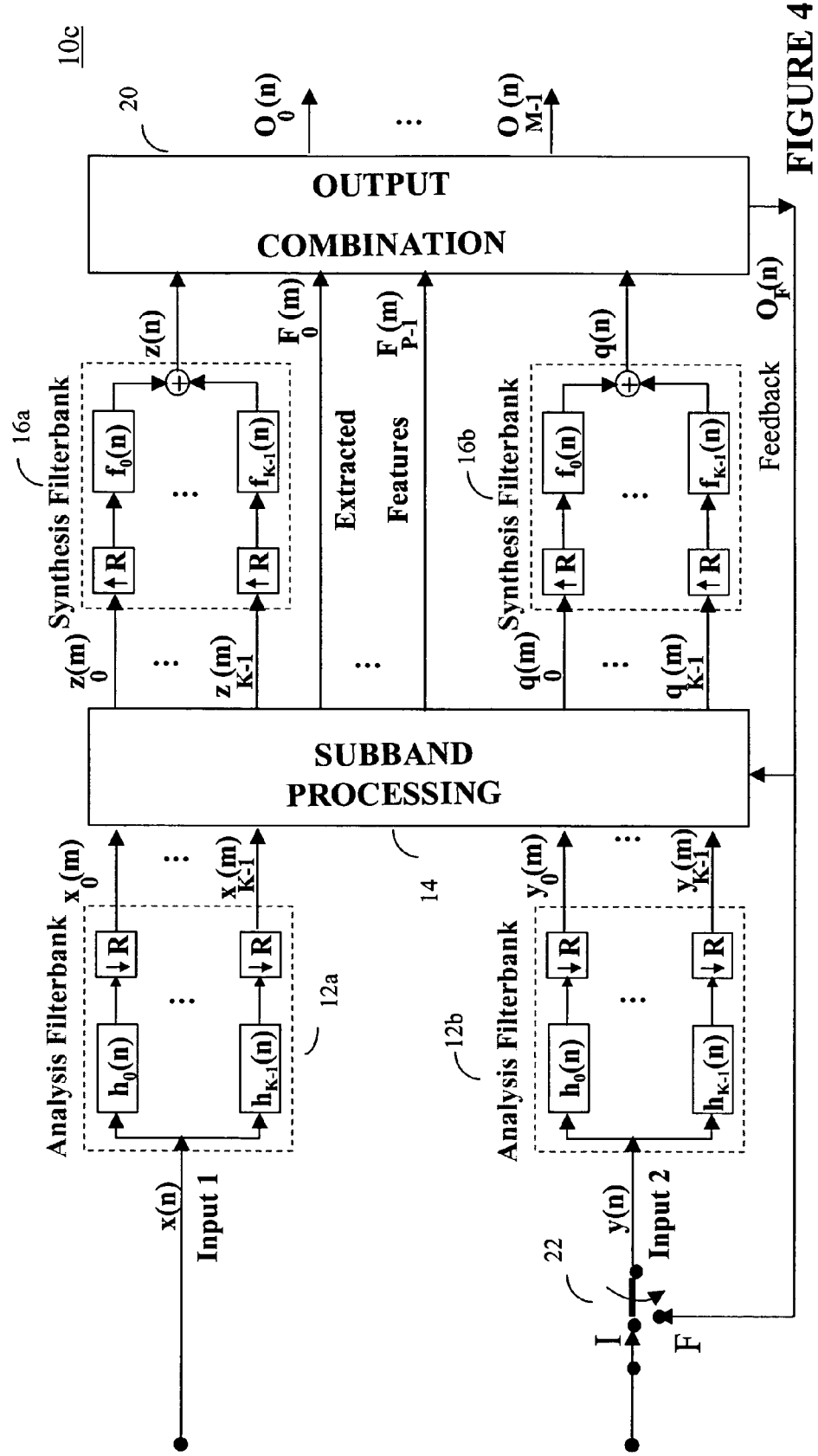
FIG. 4 is a diagram showing a physiological signal processing system in accordance with a further embodiment of the present invention.
Figure 5:
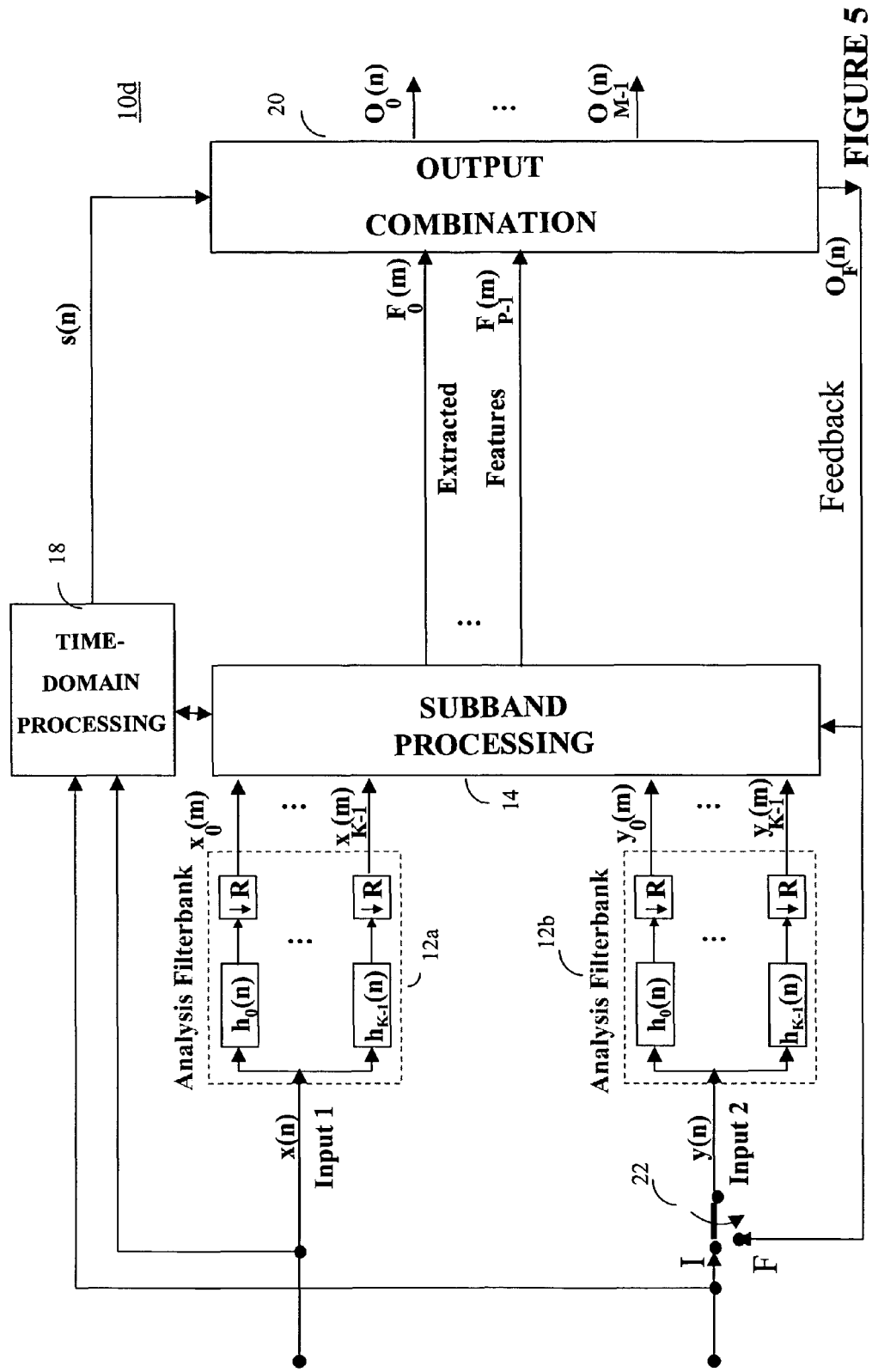
FIG. 5 is a diagram showing a physiological signal processing system in accordance with a further embodiment of the present invention.
Figure 6:
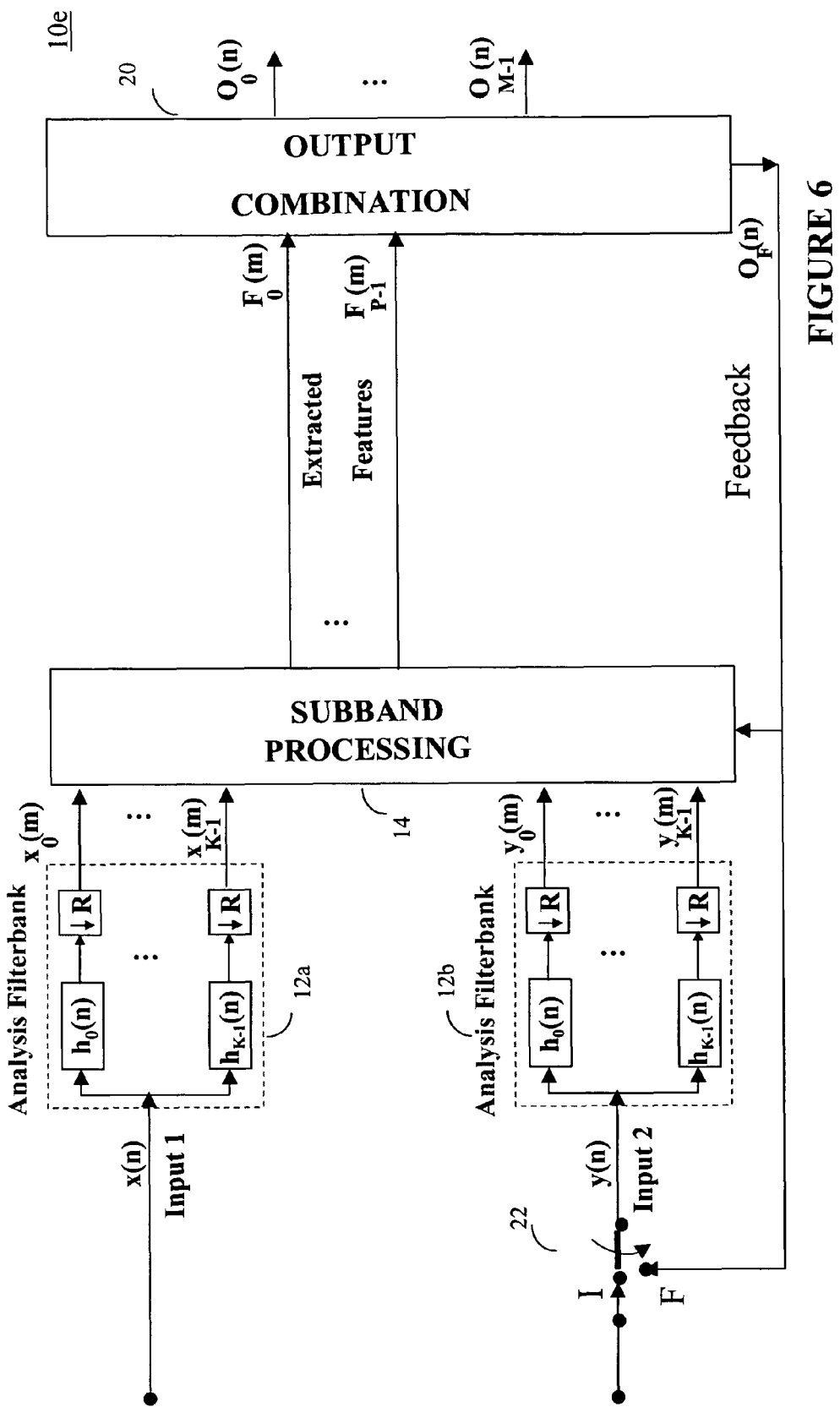
FIG. 6 is a diagram showing a physiological signal processing system in accordance with a further embodiment of the present invention.

FIG. 3 shows a physiological signal processing system 10b in accordance with a second embodiment (b) of the present invention. The system 10b is similar to the system 10a of FIG. 1 except for the over-sampled filterbanks. In system 10b, the over-sampled analysis filterbanks 12a, 12b and the over-sampled synthesis filterbanks 16a, 16b are replaced by Weighted-OverLap Add (WOLA) analysis filterbanks 26a, 26b and WOLA synthesis filterbanks 28a, 28b, respectively. The WOLA implementation offers a low-delay, flexible, and efficient implementation of the over-sampled filterbanks as described in U.S. Pat. No. 6,236,731, WO 98/47313, R. Brennan and T. Schneider, "A Flexible Filterbank Structure for Extensive Signal Manipulations in Digital Hearing Aids", *Proc. IEEE Int. Symp. Circuits and Systems*, pp. 569-572, 1998, and U.S. Pat. No. 6,240,192, which are incorporated herein by reference.

Figure 7:
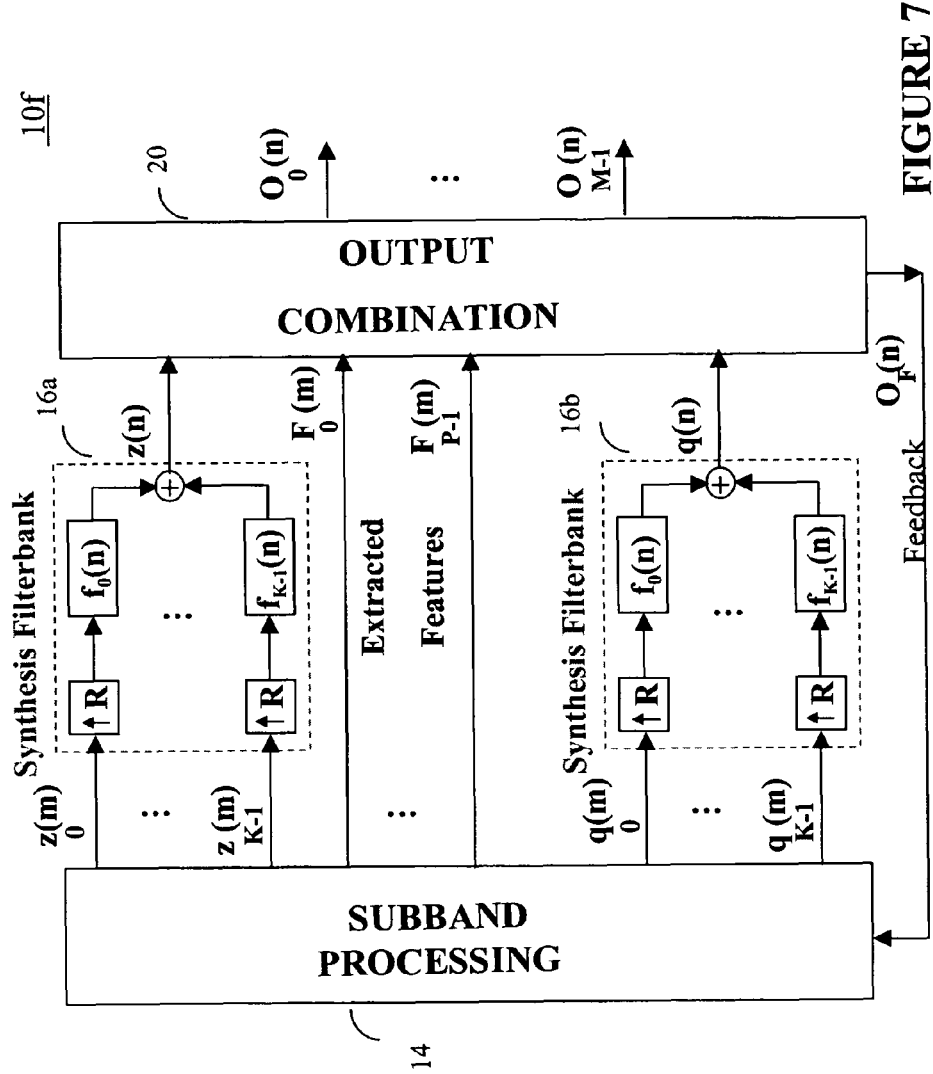
FIG. 7 is a diagram showing a physiological signal processing system in accordance with a further embodiment of the present invention.

The systems 10a and 10b may be further optimised or simplified for specific applications as long as one or more over-sampled filterbanks or WOLA analysis and/or synthesis are present in the system. FIGS. 4-7 show systems 10c-10f in accordance with further embodiments (c)-(f) of the present invention. For example, in the system 10c of FIG. 4, the time-domain processing block does not exist as it is not needed for certain applications. Similarly, synthesis filterbanks and their outputs may not be needed in some architectures, such as system 10d of FIG. 5, and system 10e of FIG. 6. An example could be heartbeat rate detection through joint time-domain and subband processing, without a need to play the heartbeat sound at the output. In the system 10e of FIG. 6, only features are extracted through the subband processing 14. An example could be heartbeat rate detection through subband processing. Finally, as shown in FIG. 7, the system 10f does not include the analysis filterbanks. The subband processing block 14 may receive, at its input, a feedback signal from the output combiner 20, a signal from the input/output storage, transmission, reception block 24 of FIG. 2, or a combination thereof. In some applications, the input signals may have been analysed and stored prior to subband processing 14. Thus, the analysis stage is not needed on-line.

The over-sampled analysis and synthesis filterbanks of the systems 10c, 10d, 10e and 10f of FIGS. 4-7 may be replaced by WOLA analysis and WOLA synthesis filterbanks, respectively.

Figure 8:
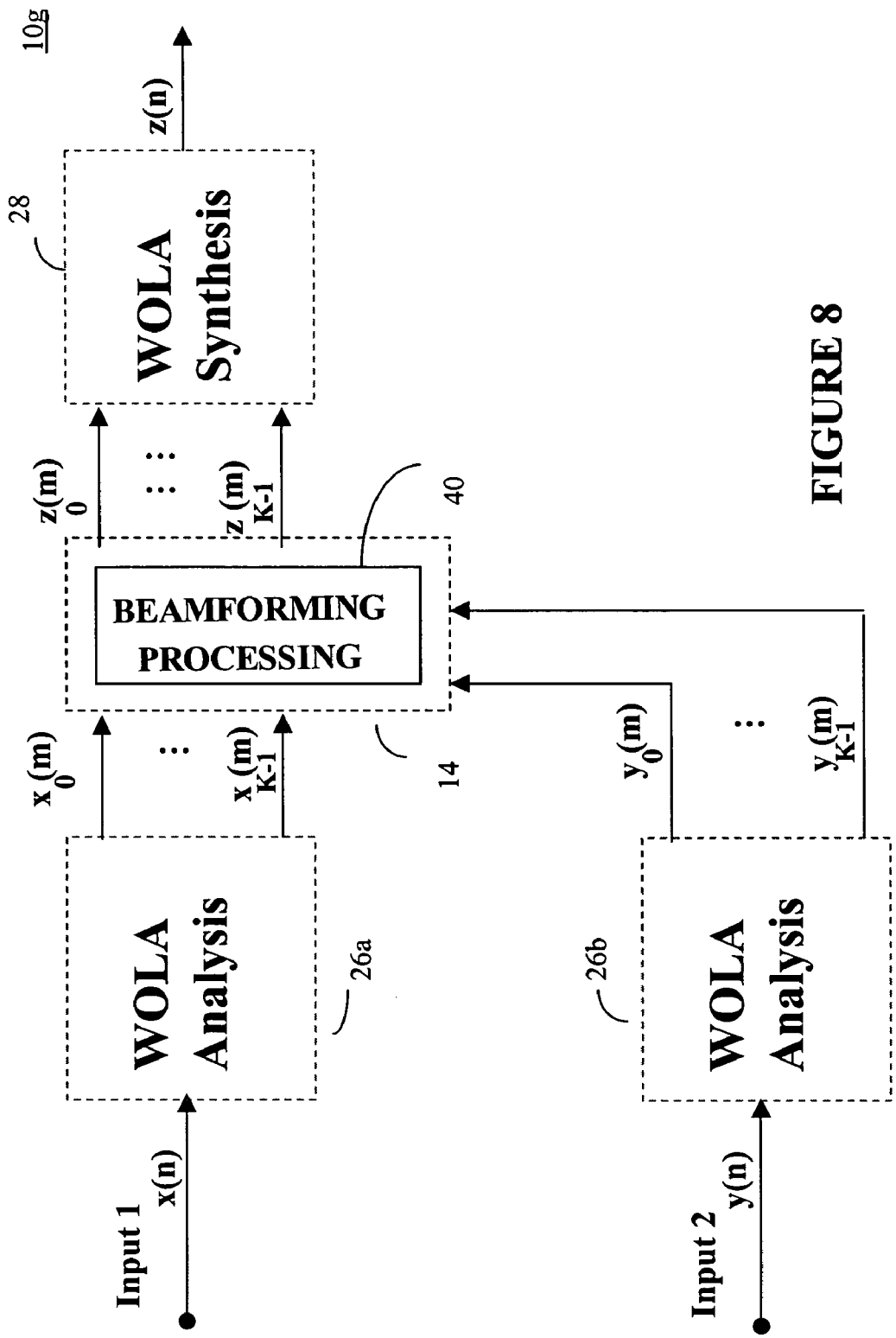
FIG. 8 is a diagram showing a physiological signal processing system with beamforming algorithm in accordance with a further embodiment of the present invention.
Figure 12:
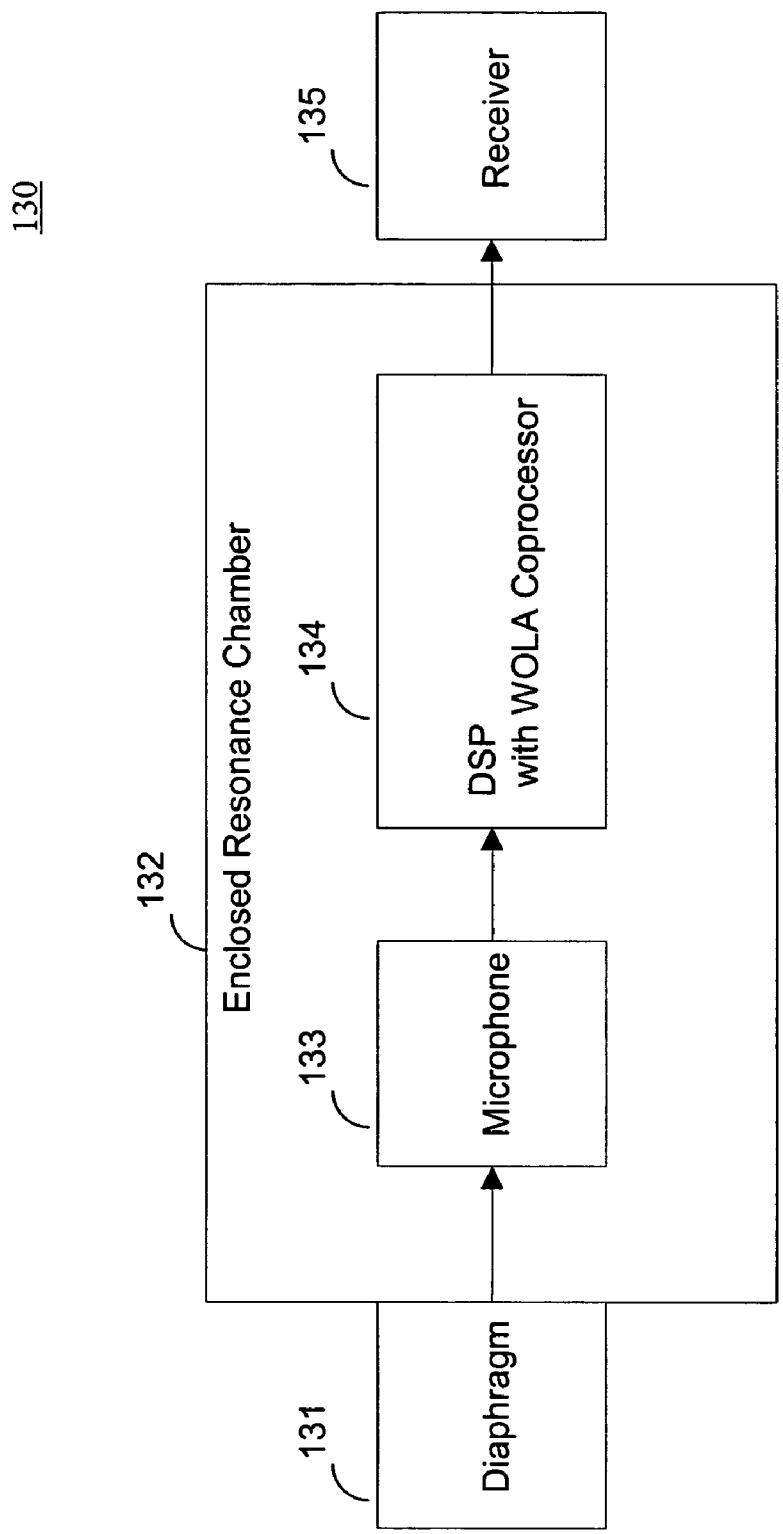
FIG. 12 is a diagram showing a stethoscope in accordance with an embodiment of the present invention.

A beamforming algorithm may be used as part of a physiological signal processing system, such as the systems 10a-10f of FIGS. 1 and 3-7. For example, when multiple sensors are employed to process various signals coming from distinctly located sources (such as mother's heartbeat and fetal heartbeat) beamforming will enable the user to aim at a particular sound source with less interference from other sources. This algorithm takes two or more input signals in the time-domain signal and converts them to the frequency-domain using either an over-sampled analysis filterbank, or a WOLA analysis filterbank. The beamforming algorithm processes the data before the signal is converted back to the time-domain by an over-sampled synthesis filterbank or a WOLA synthesis filterbank. FIG. 8 shows a physiological signal processing system 10g in accordance with a further embodiment (g) of the present invention. The system 10g contains a beamforming block 40 which performs a beamforming algorithm. The beamforming block 40 receives the outputs of the WOLA analysis filterbanks 26a, 26b and provides its output to the WOLA synthesis filterbanks 28. In FIG. 12, two inputs are provided to the system 10g. However, one or more than two inputs may be provided to the system 10g. Various beamforming algorithms have been disclosed in U.S. patent application Ser. No. 10/214,350, Publication No. 20030063759, which is incorporated herein by reference.

The WOLA analysis and synthesis filterbanks in FIG. 8 may be replaced by over-sampled analysis and synthesis filterbanks, respectively. The subband processing 14 of the physiological processing systems 10a-10g may include the beamforming processing block 40.

Figure 9:
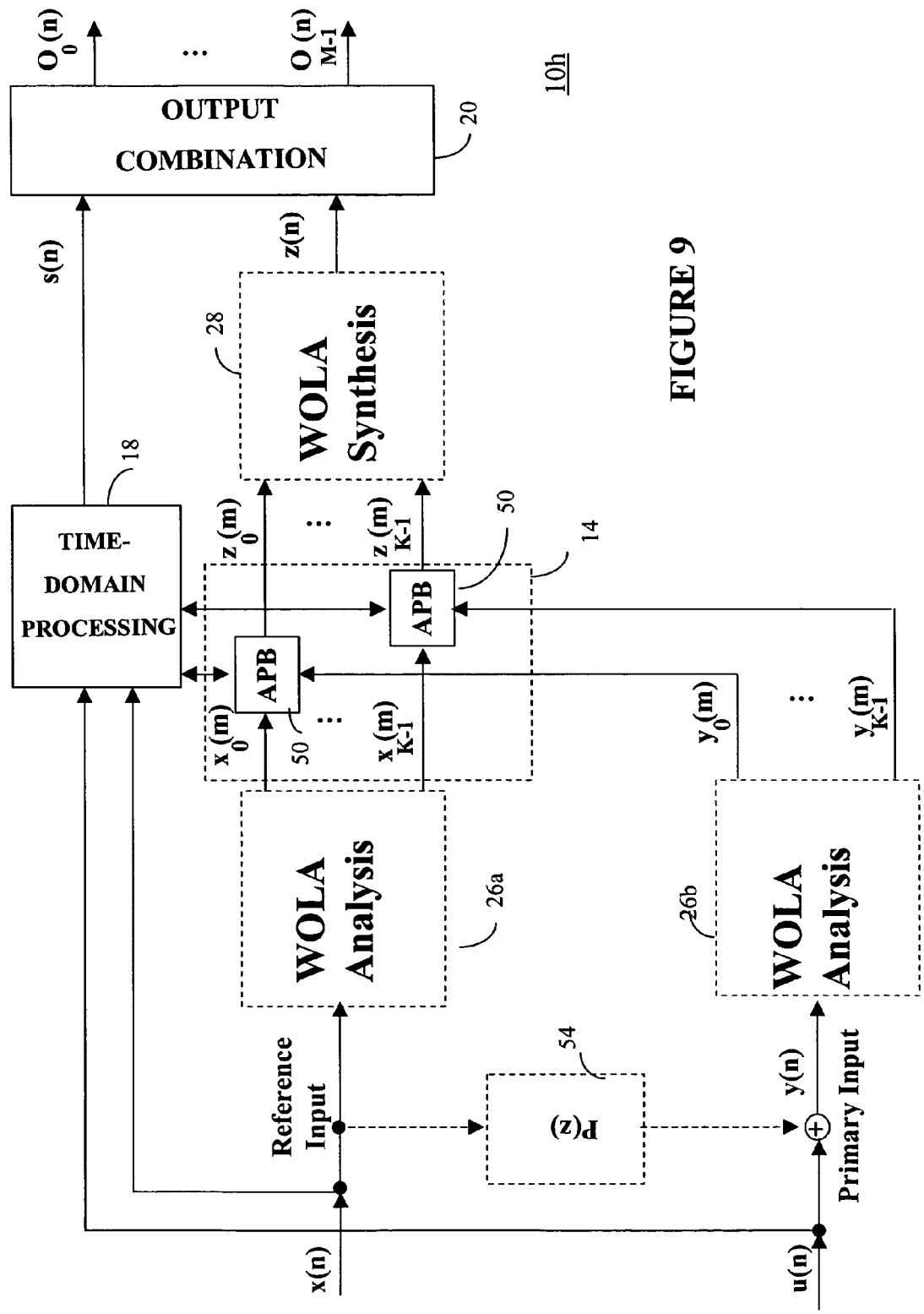
FIG. 9 is a diagram showing a physiological signal processing system with a subband adaptive filter in accordance with a further embodiment of the present invention.

Subband adaptive filtering may be implemented in a physiological signal processing system. FIG. 9 shows a physiological processing system 10h with a subband adaptive filter (SAF) in accordance with a further embodiment (h) of the present invention. In many applications, a signal (reference signal x(n) in FIG. 9) may leak into anther signal u(n) after passing through a system 54 (P(z)). The second input to the WOLA analysis 26b is the primary signal y(n) that includes u(n) plus a component correlated to x(n). SAFs can efficiently cancel the interference (X(z).P(z) in the Z-domain) by exploiting the correlation of the primary signal with the reference signal. An example is isolating lung sounds in signals containing both heart and lung sounds. This will enable the listener to hear the lung sound without the interference of other sounds. A second example would involve isolating a fetal heartbeat from a signal containing both the maternal and fetal heartbeats. This will enable the fainter fetal heartbeat to be processed separately and heard more clearly.

These examples, as well as others can be implemented in the same way using the structure shown in FIG. 9. At least two input (possibly physiological) signals (x(n) and y(n)) are converted from the time-domain to the frequency-domain using the WOLA analysis filterbank (12a, 12b). The system 10h contains Adaptive Processing Blocks (APBs) 50. Each subband is processed by the corresponding APB 50 before being synthesized by the WOLA synthesis 28. The results s(n) of the time-domain processing 18 may then be combined with the subband processing result z(n) to generate one or more output signals that are free from interference. As described above in the embodiment (a), the time-domain processing 18 may interact with the subband processing in different ways. In particular, the SAFs may be converted back to the time-domain to reconstruct a time-domain adaptive filter to be used in the time-domain processing 18. This will reduce the processing delay through the system.

The WOLA analysis and synthesis filterbanks in FIG. 9 may be replaced by over-sampled analysis and synthesis filterbanks, respectively. The physiological processing systems 10a-10g of FIGS. 1 and 3-8 may include the APBs 50. For example, APBs disclosed by U.S. patent application Ser. No.

10/642,847, Publication No. 20040071284 may be used as APB 50. The APBs (for example) employ whitening by spectral emphasis, whitening by decimation and a combination of the two, step-size adaptation techniques, as well a hybrid of subband adaptive filtering and Wiener filtering to achieve improved performances.

Figure 10:
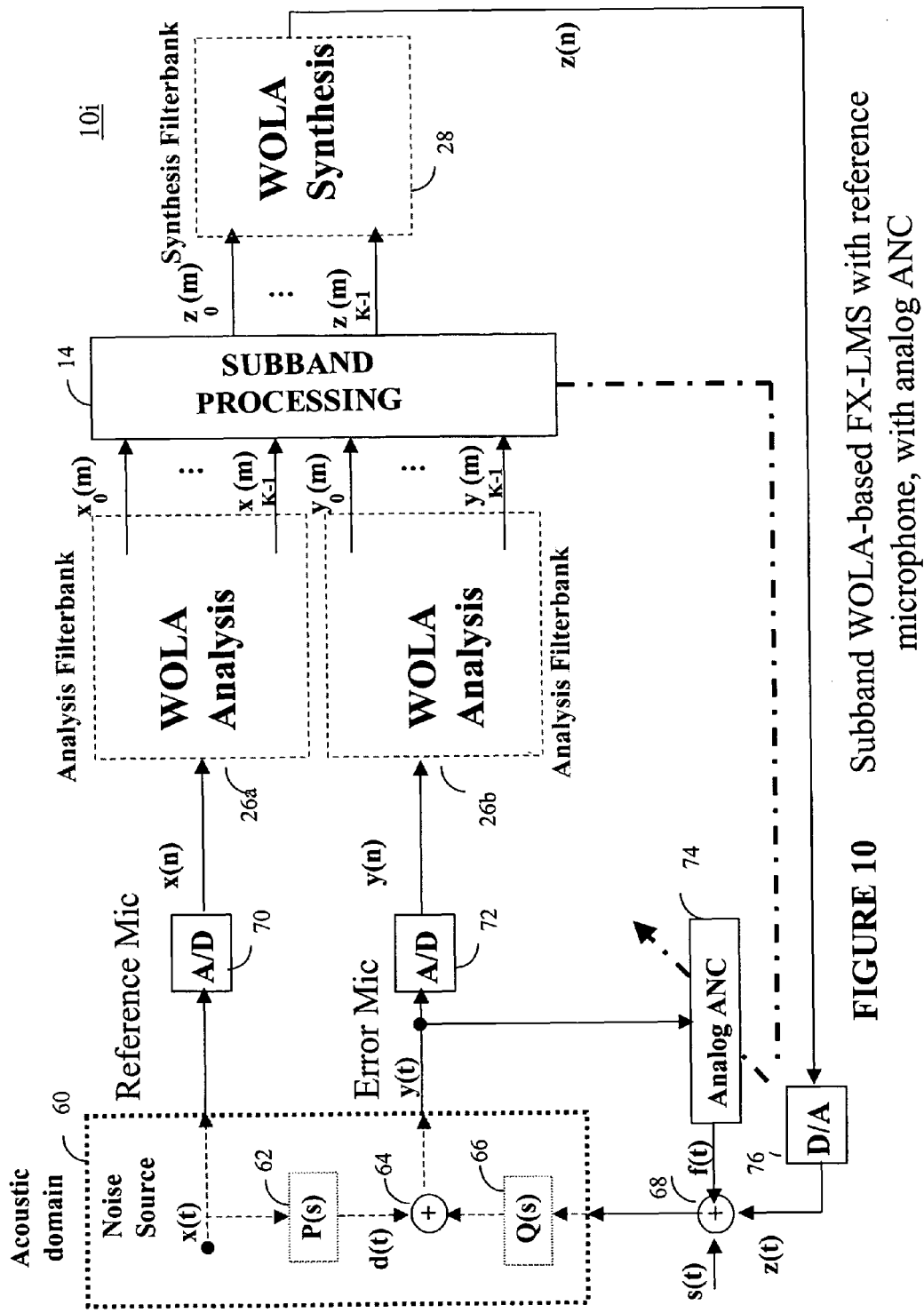
FIG. 10 is a diagram showing a physiological signal processing system with an active noise cancellation in accordance with a further embodiment of the present invention.

Active noise cancellation using over-sampled filterbank may be employed for input (possibly physiological) signals. FIG. 10 shows a physiological signal processing system 10$i$ in accordance with a further embodiment (i) of the present invention. In FIG. 10, a noise source x(t) passes through the acoustic medium (modelled by acoustic transfer function P(s), s denoting the Laplace transform variable), added to a desired signal s(t) (that has to pass through an acoustic transfer function Q(s)) and converted to an electric signal y(t) by the microphone 64 (denoted by an adder in FIG. 10). After analog to digital conversion (A/D) 70, 72, the two signals x(n) and y(n) are processed by a subband adaptive system to estimate a noise signal estimate z(n).

The system 10$i$ includes subband processing 14 that might include adaptive processing employing one of many adaptive algorithms, such as filtered-X LMS (FXLMS), Affine Projection Algorithm (APA), or Recursive Least Squares (RLS). The noise signal is then converted back to an acoustic signal, played through a noise speaker 68 to reach the microphone 64 and added acoustically to the microphone signal to cancel the additive noise. The noise speaker to microphone acoustic transfer function Q(s) 66 can be estimated offline or online to be employed in the system 10$i$. The system 10$i$ may have processing delay between the inputs (x(t) and y(t)) and the output z(t). Canadian Patent application No. 2,481,629, filed on Sep. 15, 2004, entitled "Method and system for active noise cancellation", discloses methods of reducing the delay with more efficient designs, which is incorporated herein by reference. One possible solution is to combine the subband-based Active Noise Cancellation (ANC) with an analog ANC 74 with its parameters such as loop-filter and loop-gain adjusted through subband processing as shown in FIG. 10. An example of an application of this system is a stethoscope with more than one sensor, capable of reducing interference from lungs and other noise sources into the heartbeat sound through active noise cancellation. The system 10$i$ might operate without the reference microphone 70 as described in the Canadian Patent application No. 2,481,629, filed on Sep. 15, 2004, entitled "Method and system for active noise cancellation". When a reference signal is not available, it is possible to reconstruct it in the FX-LMS or similar adaptive systems based on estimation of microphone acoustic transfer function Q(s).

In the above embodiments, each system receives two inputs. However, more than two inputs may be provided to each system.

In all embodiments, the over-sampled filterbanks may be implemented on a DSP with a WOLA coprocessor as disclosed in U.S. Pat. No. 6,236,731; WO 98/47313; R. Brennan and T. Schneider, "A Flexible Filterbank Structure for Extensive Signal Manipulations in Digital Hearing Aids", Proc. IEEE Int. Symp. Circuits and Systems, pp. 569-572, 1998; U.S. Pat. No. 6,240,192; U.S. patent application Publication No. 20030063759; U.S. patent application Publication No. 20040071284.

Figure 11:
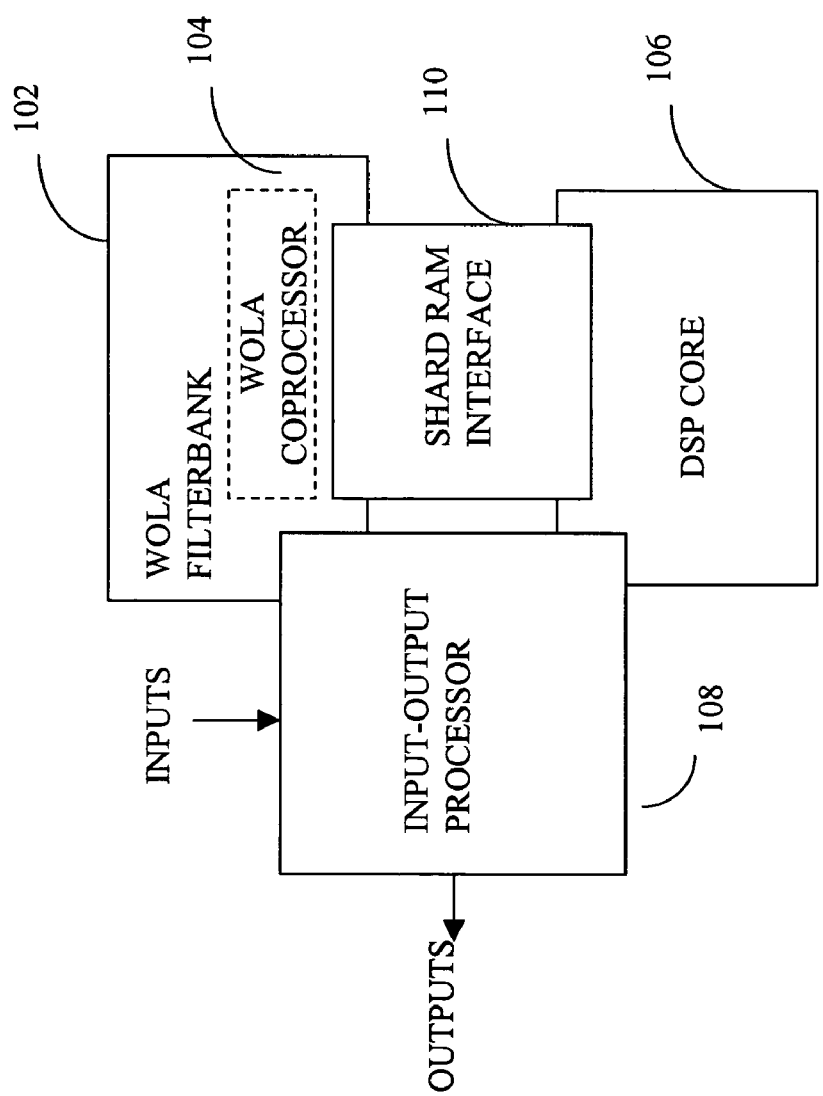
FIG. 11 is a diagram showing an example of a platform of an WOLA filterbank.

FIG. 11 illustrates an example of a platform of an WOLA filterbank. The platform 100 of FIG. 11, referred to as the DSP system 100, includes a WOLA filterbank system 102 having a WOLA coprocessor 104, a DSP core 106, and an input-output processor (IOP) 108.

The WOLA filterbank system 102, the DSP core 106, and the IOP 108 operate in parallel. The parallel operation of these components enables the implementation of complex signal processing algorithms with low system clock rates and low resource usage and is adept at subband signal processing. It may be adapted to generate critically-sampled, real-valued filterbanks for a CODEC (e.g. 194 of FIG. 15) as described below.

The WOLA filterbank 102 is microcodeable and includes "time-window" microcode to permit efficient multiplication of a waveform by a time-domain window, the WOLA filterbank 102, and data memory. The configurable WOLA coprocessor 104 efficiently splits the full band input signals into subbands, leaving the core free to perform other algorithm calculations.

For example, the WOLA coprocessor 104 may be an 18-bit block floating point WOLA filterbank coprocessor, and the DSP core 106 may be a 16-bit fixed-point DSP core.

The WOLA filterbank 152 may operate as the over-sampled WOLA filterbank as described in U.S. Pat. No. 6,236,731 and U.S. Pat. No. 6,240,192B2.

The programmable DSP core 106 enables it to implement time-domain algorithms that are not directly implementable by the WOLA coprocessor 104. This adds a degree of reconfigurability.

The IOP 108 is responsible for transferring and buffering incoming and outgoing data. The IOP 108 may receive information from analog/digital (A/D) converter (not shown). The output of the IOP 108 may be supplied to a digital/analog (D/A) converter (not shown).

RAM 110 includes two data regions for storing data of the WOLA filterbank 102 and the DSP core 106, and a program memory area for the DSP core 106. Additional shared memory (not shown) for the WOLA filterbank 102 and the IOP 108 is also provided which obviates the necessity of transferring data among the WOLA filterbank 102, the DSP core 106 and the IOP 108.

As an embodiment of the present invention patent, stethoscope for listening to physiological sounds is described in detail. A stethoscope in accordance with an embodiment of the present invention includes over-sampled filterbank which is implementable into the platform of FIG. 11.

FIG. 12 shows a stethoscope 130 in accordance with an embodiment of the present invention. The stethoscope 130 is an electronic instrument to listen to physiological sounds including heartbeats, lung sounds and bowel/gastrointestinal sounds, among others. The stethoscope 130 includes a diaphragm 131, an enclosed resonance chamber 132, and a microphone 133. The diaphragm 131 is a disk used for amplifying the sound. The microphone 133 transforms the sound in the chamber 132 from an acoustic to an electrical signal. The stethoscope 130 further includes at least one programmable digital signal processor 134 on which the WOLA coprocessor (e.g. 104 of FIG. 11) resides. The DSP system 134 corresponds to the DSP system 100 of FIG. 11. The stethoscope 130 further includes one or more receivers 135 or speakers which make the sound audible for the stethoscope wearer, and/or one or more algorithms to process one or more live input signals and/or one or more recorded signals.

The stethoscope 130 has the functionality of one or more filtering modes to emphasize different portions of the signal, and volume control. The stethoscope 130 has record functionality whereby one or more live input signals are stored in non-volatile memory such as an EEPROM. The signal may or may not be compressed prior to storage. The stethoscope 130 has playback functionality whereby one or more signals stored in non-volatile memory such as an EEPROM are played back either at the recording speed or some other speed, such as half speed. The stethoscope 130 has the functionality of a human-machine interface for controlling the functionality. For example, the interface unit has a plurality of buttons including: one to control volume up, one to control volume down, one to change the filtering mode used by the gain adjustment algorithm, one to record, one to initiate playback and one to initiate half speed playback. The interface unit has an LCD display that indicates the current filtering mode, volume changes, whether recording/playback is occurring and whether the battery is low. The interface unit commutates with the DSP system 134.

It is assumed that the DSP system (134) includes an 18-bit block floating point weighted overlap-add (WOLA) filterbank coprocessor, a 16-bit fixed-point DSP core, and an input-output processor (IOP). The parallel operation of these components enables the implementation of complex signal processing algorithms with low system clock rates and low resource usage and is particularly adept at subband signal processing. The configurable WOLA coprocessor (104 of FIG. 11) efficiently splits the full-band input signals into subbands, leaving the core free to perform other algorithm calculations.

The WOLA coprocessor (104 of FIG. 11) implements a flexible over-sampled Generalized DFT (GDFT) filterbank. It may be adapted to generate critically-sampled, real-valued filterbanks as required for a codec in this application It is assumed that the algorithms are implemented on the DSP system 134 using a 16-band, 4-times over-sampled WOLA filterbank configuration with odd-stacking. The selected configuration generates a group delay of 17 milliseconds, has a system clock frequency of 5.12 MHz and a sampling frequency of 8 kHz. This is one configuration, and others are also possible.

Figure 13:
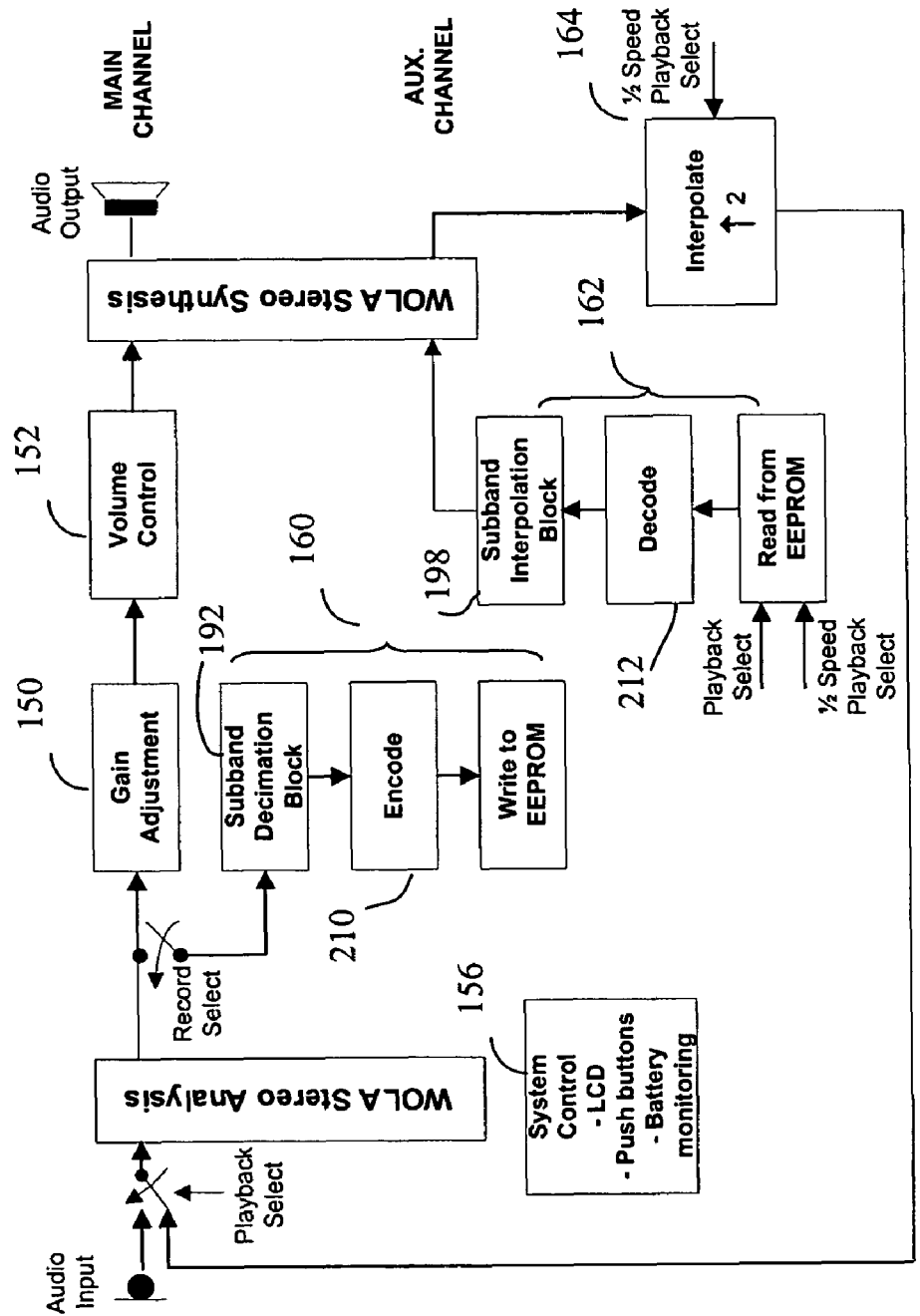
FIG. 13 is a diagram showing an example of the stethoscope of FIG. 12.

FIG. 13 illustrates examples of the stethoscope 130 of FIG. 12.

Referring to FIG. 13, the stethoscope includes a plurality of modules including module 150 for subband gain adjustment, module 160 for record functionality, modules 162 and 164 for playback functionality and playback at half speed functionality, and system-level features including volume control module 152 and control module 156 for battery monitoring, push buttons control and a LCD display. Blocks 150, 152, 160, and 162 are examples of possible subband processing 14 in FIG. 1. Block 164 is an example of possible output combination in FIG. 1.

The subband gain adjustment algorithm 150 provides frequency shaping as required by the various listening modes. Generally, the components of heartbeat and lung sounds useful for diagnostic purposes are in the range of 20-1000 Hz. The first through fourth heart sounds fall in the range of 20-115 Hz. Disorders such as pulmonary and aortic diastolic heart murmurs occur in the range of 140-600 Hz. Thus, a suitable listening range for heart sounds is approximately 20-600 Hz. For breathing sounds, the strongest part of the signal is typically under 100 Hz, although the signal can have useful components up to 1.2 kHz.

As described below, the subband codec (e.g. 194 of FIG. 15) is used as part of the record and playback functionality. During recording, the signal is captured, encoded, packed and written to non-volatile memory (e.g. EEPROM) (160). During playback, the packed signal is read from the EEPROM, unpacked, decoded and re-synthesized in real-time (162). Interpolation module 164 is provided for half speed playback mode.

The filterbank requirements of the subband gain adjustment algorithm and the subband coding algorithm are different. Subband gain adjustment requires low delay and yet optimal filter responses to reduce the level of uncancelled aliasing that is generated when gains are varied in different subbands. The WOLA filterbank uses over-sampling to achieve high levels of aliasing reduction without increasing the filter length and consequently the group delay as described in U.S. Pat. No. 6,236,731. To keep the group delay as low as possible, as an example, a sampling frequency of 8 kHz is selected. A sampling frequency of 4 kHz is more appropriate given the bandwidth of heart and lung sounds, but has higher group delay. The gain adjustments required by the different listening modes are large Thus, an over-sampling factor of at least 4 may be selected to minimize group delay and minimize aliasing artifacts.

In contrast, the subband coding algorithm requires a critically-sampled, real-valued filterbank to achieve minimal data rates. Low group delay is not a requirement. As described in D. Hermann et al. ("Low-Power Implementation of the Bluetooth Subband Audio Codec", Proc. ICASSP 2004), critically-sampled, real-valued subband signals can be obtained by postprocessing and decimating the over-sampled complex WOLA subband signals.

In order to design the WOLA filterbank having relatively low group delay and an over-sampling factor of 4, an analysis window length (La) of 128 samples, a synthesis window length (Ls) of 128 samples, an input block size of R=8 samples and an FFT size of N=32 may be selected. This is an exemplary configuration. Other configurations are also possible.

For subband gain adjustment algorithm, the system 130 may implement three different filter modes which have been designed based upon the characteristics of heart and lung sounds: a bell mode, which amplifies low frequency heart sounds in the range 0-500 Hz, a diaphragm mode, which amplifies lung sounds in the range 0-1000 Hz and an extended range mode which amplifies sounds between 0-1500 Hz.

The use of an over-sampled subband filterbank permits the application of efficient gain adjustments. The gain application is a vector process in which each subband is multiplied by a real-valued gain. In this system, the gain application process occurs on dedicated, efficient hardware, namely, the WOLA coprocessor (104 of FIG. 11).

The number of subbands used in the stethoscope design is, for example, 16. This number directly determines the resolution of the frequency shaping. Since the sampling frequency is 8 kHz, the bandwidth of each band is 250 Hz. The system utilizes odd-stacking which means that the first band encompasses the frequencies from 0 to 250 Hz. A real-valued gain is provided for each band. To implement the bell mode, for example, gains greater than zero are provided for the first two subbands while gains of zero are provided for the remaining subbands.

One possible codec (e.g. 194 of FIG. 15) uses adaptive PCM quantization in each subband. This quantization scheme was used because it provides good performance for slowly varying signals such as heart sounds, while having a low complexity implementation. Other quantization schemes may be used. This subband codec requires critically-sampled, real-valued subband signals as input. Since the filterbank required by the gain adjustment algorithm has an over-sampling factor of 4, for example, the analysis results are downsampled by a factor of 2 and then converted to cosine modulated filterbank results in order to be usable by the codec. The analysis filterbank applicable to the subband codec has the form described by Equation (1), where hm(n) is the subband analysis filter, m is the subband index, M=16 is the number of subbands and hp(n) is the prototype low-pass filter. The filter length, L was set to La=Ls. Note that this filterbank, referred to as a cosine-modulated filterbank, uses odd-stacking and that the WOLA filterbank is also configured for odd-stacking. Other filterbank configurations are possible.

$$h_m(n) = h_p(n)\cos\left[\frac{\pi}{M}\left(m+\frac{1}{2}\right)\left(n-\frac{M}{2}\right)\right] \quad n = 0 \cdots L-1 \quad (1)$$

To achieve this filterbank of (1), the following two steps are implemented. First, to reduce the data by a factor of 2, every other input block is skipped. This effectively doubles the block size (R) of the resulting analysis. The resulting subband signals do not contain additional aliased images because the original over-sampled subband signal is band-limited to $\pi/4$. Secondly, to obtain critically-sampled, real-valued data, the subband signals are further decimated and modulated to obtain a cosine-modulated filterbank similar to the one described in the D. Hermann reference.

The decimation of the signal before coding may cause the aliasing that is amplified by the gain adjustment 150 to appear as audible distortion during playback. To eliminate this distortion, the reconstructed signals are filtered prior to gain adjustment removing the unwanted aliasing. A filter may be implemented on the DSP core (106 of FIG. 11). However, the data may be synthesized and re-analyzed using another over-sampled filterbank prior to gain adjustment. This approach can be achieved by using a second channel that is available on the DSP, as shown in FIG. 13.

In FIG. 13, analysis results in the main channel are decimated, encoded, packed and stored 160 during the record operation. During playback, these signals are unpacked, decoded and interpolated 162 into an auxiliary channel. The reconstructed signals are synthesized in this auxiliary channel and then copied from the output of this channel to the input of the main channel. The auxiliary channel is used only for reconstruction of the encoded signal.

This two-channel approach is selected because the two separate analysis and synthesis chains are more efficiently implemented on two channels than two completely separate filterbanks are on a single channel. In order to implement two separate filterbanks on one channel, the extra synthesis and analysis steps may be implemented manually on the DSP core (106 of FIG. 11). In contrast, the chosen method takes advantage of available capabilities on the WOLA coprocessor (104 of FIG. 11) while minimally increasing resource usage.

Half speed playback functionality is described in detail. This mode requires data to be decoded at one rate and played back at another, in an architecture that has a fixed sampling rate. Halving the speed of a signal doubles the amount of the data to be processed. It is preferable to solve the problem in real-time by changing the effective sampling rate of the recorded data while playing it back at the normal fixed sampling rate.

The playback speed is halved by interpolating the decoded signal by a factor of 2 in the time domain while keeping the system's sampling rate constant. Although this interpolation method does not preserve the pitch of the signal (it is halved), the details in the sounds are more clearly heard by the medical professional in this mode. Interpolation of the time domain signal will create an image of the entire spectrum. The gain adjustment algorithm, which is performed immediately before synthesis, removes the top half of the spectrum. Thus, the gain adjustment algorithm that is already in place can be used to eliminate this imaging.

Figure 14:
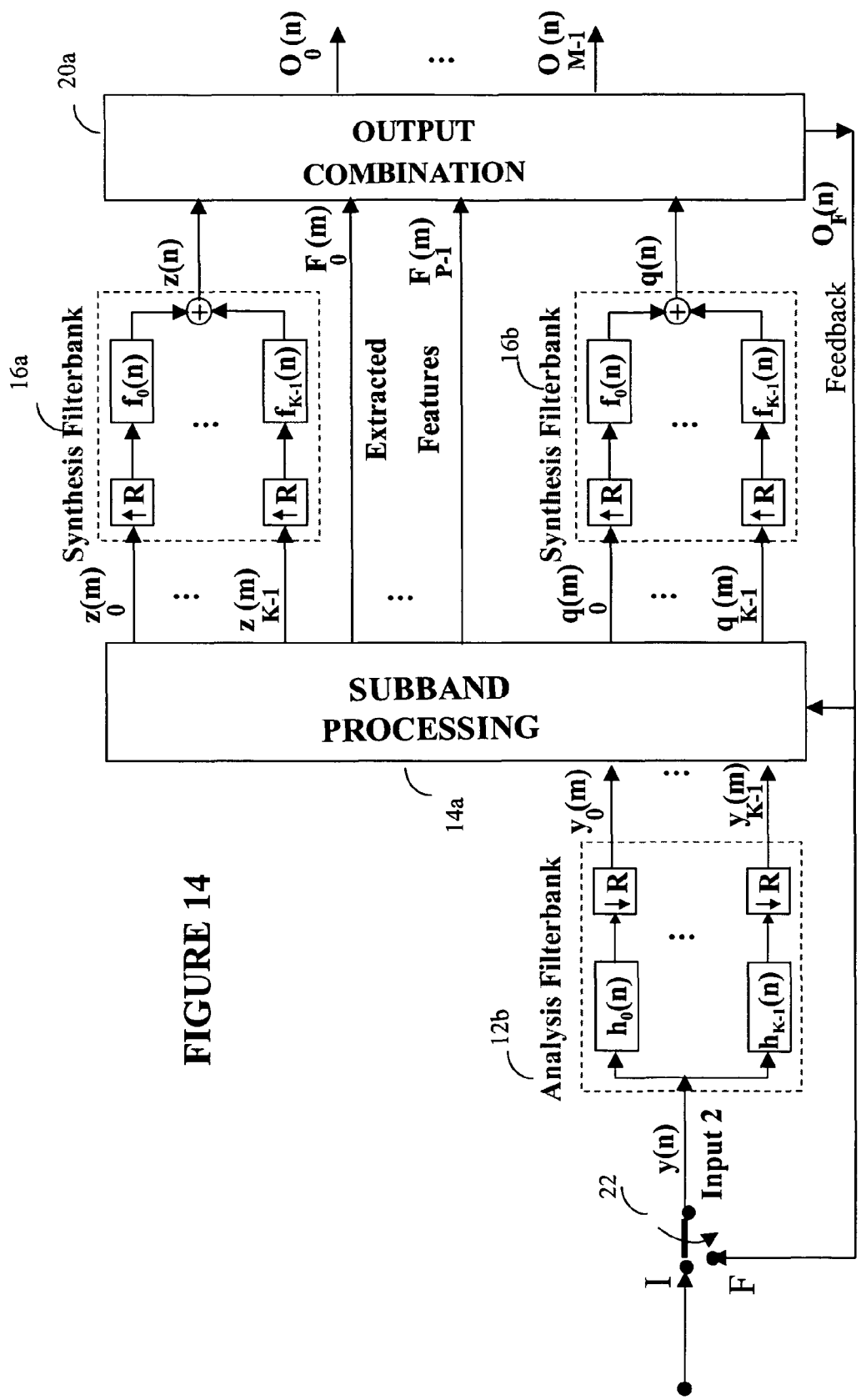
FIG. 14 is a diagram showing a possible implementation of a signal processing scheme on the DSP of FIG. 12.
Figure 15:
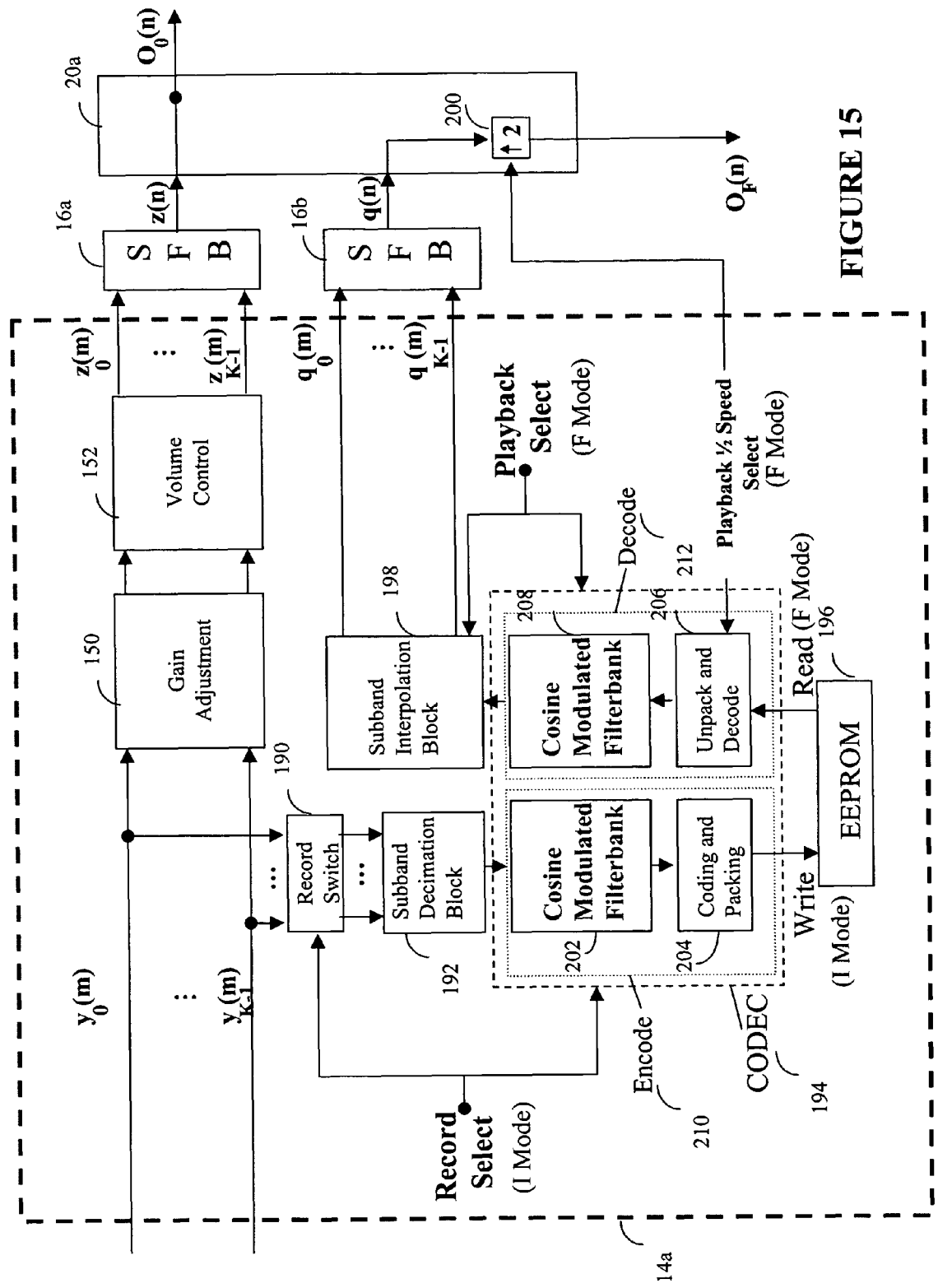
FIG. 15 is a diagram showing an example of a subband processing block and an output combination block of FIG. 14.

FIG. 14 illustrates an exemplary implementation of a signal processing scheme on the DSP with WOLA coprocessor 134 of FIG. 12. FIG. 15 illustrates the subband processing 14a and the output combiner 20a of FIG. 14. FIG. 14 employs methods of FIG. 13 for stethoscope applications.

Referring to FIGS. 14-15, the analysis filter bank 12b, a subband processing block 14a, the over-sampled synthesis filterbanks 16a-16b and an output combiner 20a are implemented on the DSP with WOLA coprocessor (134). The system of FIG. 14 accepts only one input signal y(n). It is noted that the subband processing block 14a and the output combiner 20a are similar to the subband processing block 14 and the output combiner 20 of FIG. 1.

The record, playback and playback at half speed module includes a record switch 190, a subband decimation block 192, CODEC 194, an EEPROM 196, and a subband interpolation block 198. The combiner 20a includes the interpolation module 200.

The CODEC 194 includes a cosine modulated filterbank module 202, coding and packing module 204, unpacking and decoding module 206 and a cosine modulated filterbank module 208. The cosine modulated filterbank module 202 applies cosine modulated filterbank as described above. The cosine modulated filterbank module 208 implements the inverse operation (as described in the D. Hermann reference).

The coding and packing module 204 codes data as described above, and then packs the data into frames. The unpacking and decoding module 206 unpacks the data frame and decodes the data. The decoding reconstructs the samples based on the process described above.

When the switch 22 is in the "I" position, the stethoscope (130) is in input mode and can possibly record a signal if the record switch 190 is closed by a record select input. When the switch 22 is on the "F" position, the system is in playback mode. The subband CODEC 194 is used as part of record and playback functionality. Regardless of the I/F switch position, the input signal y(n) is captured and analyzed by the over-sampled filterbank 12b. The subband analysis results $y_i(m)$, i=0, 12, . . . , K−1 are fed into the subband processing block 14a, processed by the gain adjustment module 150 and the volume control module 152. The processed signals output from the volume control module 152 are synthesized in real-time at SFB 16a to obtain the time-domain signal z(n) that is routed to the output signal $O_0(n)$. At the same time, if the record select input is active, the subband analysis results $y_i(m)$, i=0, 12, . . . , K−1 are decimated by the subband decimation module 92, converted to cosine modulated filterbank results, encoded and packed by the CODEC 194, and stored in the EEPROM 196.

During playback, compressed signals are read from the EEPROM 196, decoded and converted to oversampled, complex modulated filterbank results by the CODEC 194, and interpolated by 2 in the subband interpolation module 98 to obtain the subband signal set of $q_i(m)$, i=0, 12, . . . , K−1. This set is synthesized in real-time through the synthesis filterbank 16b to obtain the time-domain signal q(n). The signal q(n) is routed to the feedback signal $O_F(n)$ through the module 200. With the I/F switch 22 in the "F" mode, the feedback signal is analyzed by the analysis filterbank 12b prior to gain adjustment and volume control at 150 and 152. This feedback scheme is designed to eliminate distortions due to subband decimation/interpolation combined with the gain adjustment 150. After synthesis by block 16a, the signal z(n) is routed to the output signal $O_0(n)$ through the block 200. As a result, every block of data read from the EEPROM 196 is synthesized with one block (i.e. one subband sample) of delay.

While a block of data is read from the EEPROM 196, the previous block of data has already gone through the feedback loop, and is in the process of being sent to the output.

FIG. 16-18 illustrates the prototype of the stethoscope 130 of FIG. 12.

The systems 10a-10f are applicable to heart beat detection. The heart beat detection may be implemented using autocorrelation on the WOLA. This method uses a subband autocorrelation technique to detect the heartbeats.

Estimating the autocorrelation by FIR method is described in detail. First, a signal is windowed to obtain a large enough record. For example, it is windowed to have 2-4 periods of the signal included. As the minimum heart rate is around 40 beats per minute (BPM), a window of 4 seconds may be chosen. Then, the autocorrelation estimate is found directly by time-domain (autocorrelation or covariance methods) implementation using one or more complex subband signals resulting from a WOLA analysis. Finally, the peak autocorrelation value in the region of interest is found.

Assuming a window of B samples with no overlap between the windows, and A autocorrelation lags, this needs A.B complex Complex Multiply-and-Adds (CM&A's) per window, or A CM&As per sample. Typical numbers for WOLA subband implementation with a sampling frequency (Fs) of Fs=8 kHz, and R=8 are: B=4000 samples (4 seconds); Minimum and Maximum heartbeats of 40 and 250 BPMs; Autocorrelation lag range: 240-1500, thus A=1500-240=1260; Computation cost: O=A CM&A's per sample, O=1260 CM&As every ms (sample rate in subband is Fs/R=1 kHz) or 4 A (5040) real M&As per ms. Additionally, to find the squared magnitude of the autocorrelation estimate, 2*A/B extra (real) M&As: 0.002*A M&As per sample is used. This load is negligible compared to the O=A cost.

Estimating the autocorrelation by IIR method is described in detail. In IIR method, estimating the autocorrelation using sample estimation and averaging it over time is implemented by an IIR filter:

$$R(m,n)=\text{Alpha}.R(m,n-\text{Delta})+(1-\text{Alpha}).X(n).X^*(n-\text{Delta}) \quad (2)$$

where * represent complex conjugation, m represents the autocorrelation lag, n is the time index, Alpha is a constant close to one, R(m,n) is the estimated autocorrelation vector at time n, X(n) is a complex subband signal after a WOLA analysis (typically the first subband is used for heartbeat detection) and Delta>1 is a constant that controls the recursion update.

Computation cost is: O=2.A/Delta CM&As (8.A/Delta M&As) per subband sample. Delta can be chosen large enough to decrease the computations. Trade offs in choosing Delta will be described below. Typical numbers for the same WOLA parameters as the FIR method are as follows:

Delta=8 (⅛ ms), thus O=A/4=315 CM&As per sample or 1260 M&As per sample. As described above, the IIR method may be more efficient by a factor of Delta/2.

Equation (2) can be modified to:

$$|R(m,n)|=\text{Alpha}.|R(m,n-\text{Delta})|+(1-\text{Alpha}).|X(n).X^*(n-\text{Delta})| \quad (3)$$

The computation cost may be the same: O=8.A/Delta M&As per sample. However, this method needs to store only real values of the autocorrelation estimates in the range of R(m,n) to R(m,n−Delta). The autocorrelation storage needed for Equation (3) is: A.Delta as compared to 2A.Delta for Equation (2). Moreover, averaging the magnitudes estimates in Equation (3) is more efficient since it ignores the unnecessary phase.

Both IIR and FIR methods need storage for the past values of subband samples X(m,n−Delta). While the FIR methods needs to store B (4000) complex past values, the IIR method needs A (1260) complex values to be stored.

In both methods it is possible to use only the real part of the subband signal to reduce computation and storage in half. Equation (3) may be then modified as:

$$R(m,n)=\text{Alpha}.R(m,n-\text{Delta})+(1-\text{Alpha}).|\text{real}(X(n)).\text{real}(X(n-\text{Delta}))| \quad (4)$$

FIGS. 19-24 illustrate simulation results of the FIR method and the IIR method of Equation (3) for various abnormal heart sounds. In FIGS. 20-25, symbols "o" and "*" specify the IIR and FIR methods, respectively.

Figure 19:
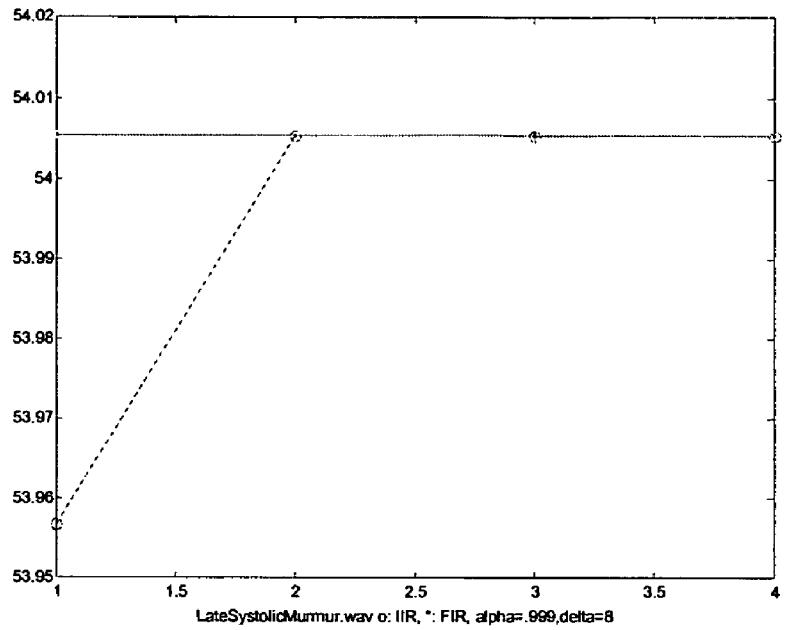
FIG. 19-24 are graphs showing simulation results associated with autocorrelation for detecting physiological signals.

FIG. 19 illustrates detected heartbeat versus time using the FIR method and the IIR method of Equation (3), for Late Systolic Murmur case.

Figure 20:
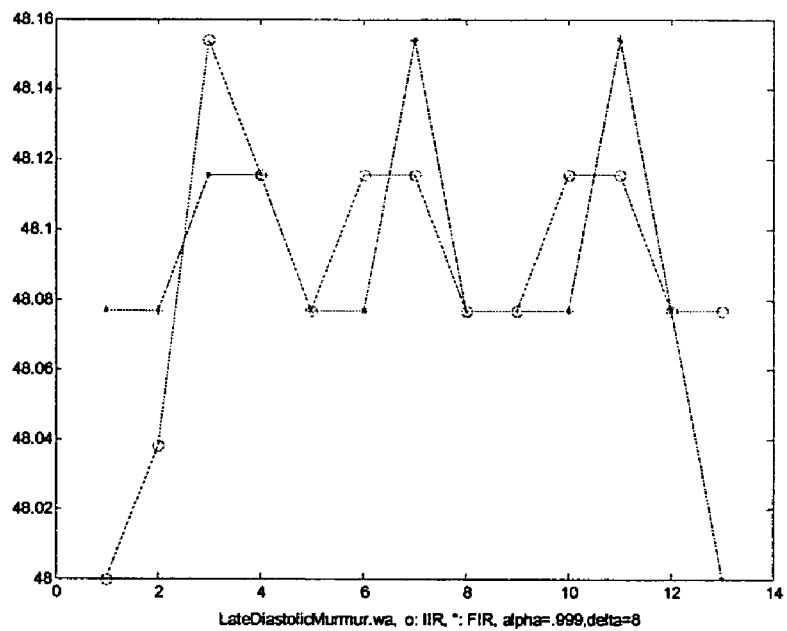

FIG. 20 illustrates detected heartbeat versus time using the FIR method and the IIR method of Equation (3), for Late Diasystolic Murmur case.

Figure 21:
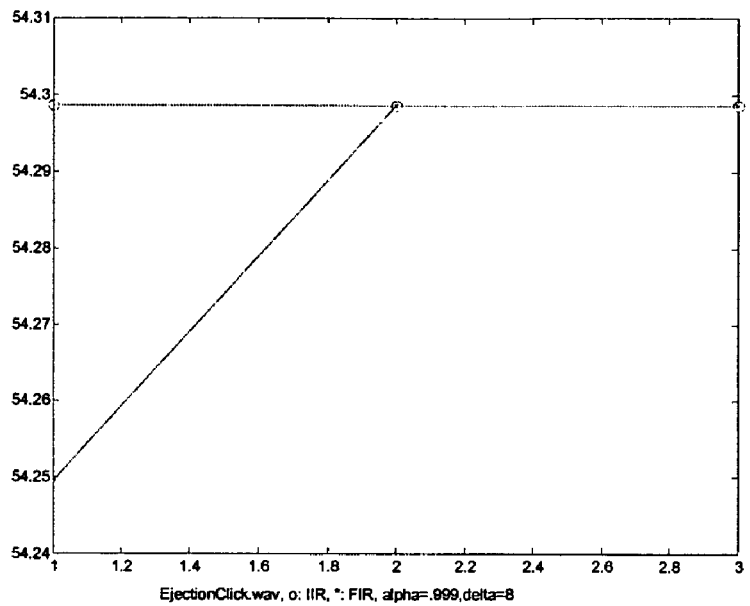

FIG. 21 illustrates detected heartbeat versus time using the FIR method and the IIR method of Equation (3), for Ejection Click case.

Figure 22:
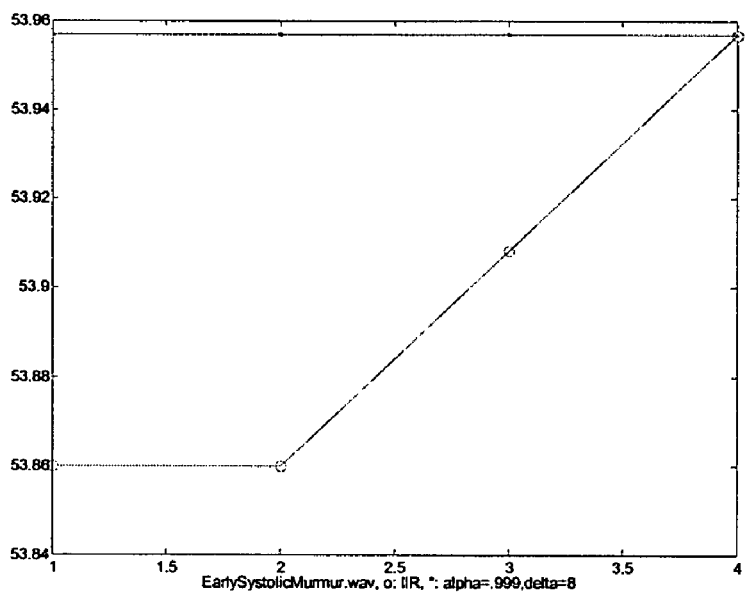

FIG. 22 illustrates detected heartbeat versus time using the FIR method and the IIR method of Equation (3), for Early Systolic case.

Figure 23:
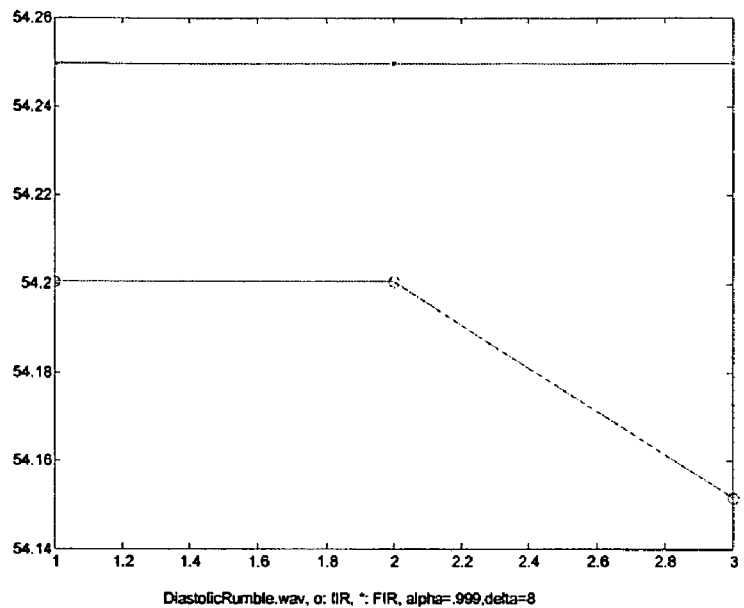

FIG. 23 illustrates detected heartbeat versus time using the FIR method and the IIR method of Equation (3), for Diastolic Rumble case.

Figure 24:
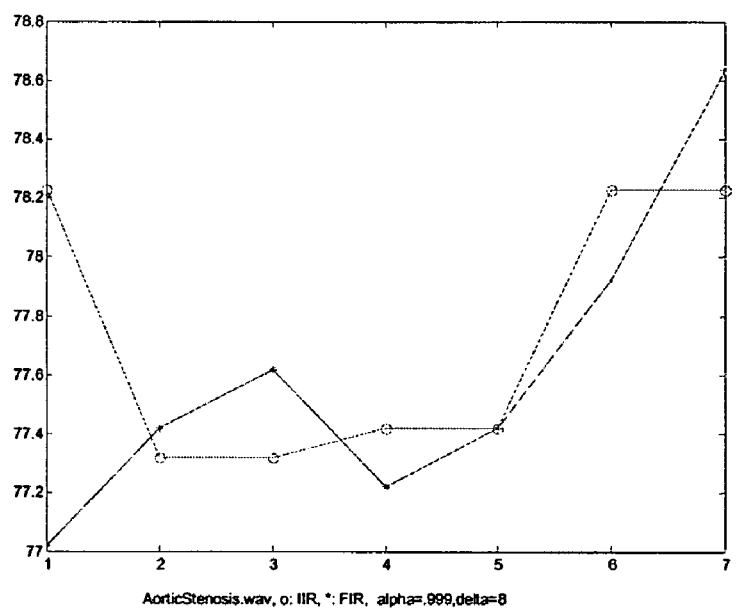

FIG. 24 illustrates detected heartbeat versus time using the FIR method and the IIR method of Equation (3), for Aortic Stenosis case.

In the simulations, the heartbeat was detected from the pre-recorded data, for various hear diseases. The FIR method and the IIR method of Equation (3) were employed with more than 30 records of heartbeats. WOLA subband signal in the first subband was employed with Fs=8 kHz, and R=8. A Power-Complementary analysis/synthesis window with L=128, N=32, and odd-stacking was used. Time window length was B=4000 samples (4 seconds), Minimum and Maximum heartbeats where 40 and 250 BPMs (Autocorrelation lag range: 240-1500). Delta=8 was used.

The heartbeat results for the FIR and IIR methods are almost identical for all test cases. The difference in heartbeat estimates is always less than one BPM.

As Delta increases, more variability of the heart beat estimate is observed. Values of Delta>8, lead to more than 1 BPM difference between the FIR and IIR estimates due to sluggish update of the recursion in Equation (3). However, up to Delta=16, the differences are still negligible.

In the simulations, Alpha was set to $$\text{Alpha}=1-1/(B/\text{Delta}) \quad (5)$$

To obtain (5), the time-constant of the exponential window, implied by the IIR method, is set to be equal to B:

$$\text{Tau}=1/(1-\text{Alpha})=B \rightarrow \text{Alpha}=1-1/B.$$

The term Delta was included to compensate for less frequent updates when Delta>1 to maintain the same implied window length for both methods.

For heartbeat detection, Adaptive Line Enhancement (ALE) may be implemented. The ALE method uses an adaptive filter with one input. The primary input is delayed by a fixed delay in the adaptive system. This is known to enhance the estimation of periodic signals. A low order (order 1 to 3) ALE may be used in just one subband with a delay of 100-200 samples in subband. To implement the ALE method, "Subband Adaptive Filtering (SAF) by Normalized Least Mean Square (NLMS)" (SAF-NLMS) method is utilized. The SAF-NLMS method is an effective adaptive filtering method designed to be implemented in subbands, for example, after WOLA analysis. For example, the SAF-NLMS may be implemented at the DSP core 106 of FIG. 11.

The processing methods and systems in accordance with the embodiments of the present invention can be efficiently deployed on a DSP hardware platform. The method and systems in accordance with the embodiments of the present invention can be efficiently implemented on the low-resource system architecture of U.S. Pat. No. 6,236,731 and WO 98/47313.

The processing methods and systems in accordance with the embodiments of the present invention have the following characteristics:

Low memory usage and low computation load and complexity.
Low processing time for signal synthesis.
Low communication bandwidth between the system and external systems (which results in low power).
Allow parallel processing, and thereby faster implementations, facilitated by decomposing the signal into subbands.
Permit proper task partitioning of necessary processing that can be implemented in an embedded system.
Allow near-orthogonal processing in each subband (for example, to tune parameters and to do processing in each subband independently or to process only relevant bands). Near-orthogonal subband signals do not materially interact with each other allowing the subband signals to be treated independently.
Employ the efficient WOLA implementation of over-sampled filterbanks.
Rather than using floating-point, it allows less expensive alternatives including block floating-point processing (fixed-point hardware in combination with data-growth exponent control) for demanding applications and pure fixed-point processing for less demanding applications (combinations of block floating-point and fixed-point are of course included).
Allow better algorithm development framework through the exploitation of efficient subband processing enabling more complex algorithms to be deployed, leading to higher quality processing, better audio output and better feature extraction.

The processing methods and systems in accordance with the embodiments of the present invention offers the following advantages:

Ultra-low power and small size leading to increased portability and battery life.
Low delay.
Executes complex processing in real-time providing higher quality outputs (audio and otherwise).
Provides more robust feature extraction.
Fit to the user/wearer properly.

The physiological signal processing in accordance with the embodiments of the present invention is applicable in a wide range of technology areas including heartbeat and lung signal analysis/synthesis provided by stethoscopes or ECG devices, processing EMG signals or other time-domain input signals.

The physiological signal processing on an ultra-low resource platform can extend the range of applications for medical technology due to its high performance, low-power consumption and small size. The physiological signal processing system described above is particularly useful in environments where power consumption must be reduced to a minimum or where an embedded processor in a portable system does not have sufficient capabilities to process the signal. For example, it could be used in on-line heartbeat detection on electronic stethoscopes where a low-resource subband processor receives the heartbeat and lung signals directly from microphones, analyses the signals in subband to separate various signals, robustly detects their features (such as heartbeat rate), cancels undesired interferences and synthesizes the signals in an efficient manner without increasing the size or weight of the stethoscope.

All citations are hereby incorporated by reference.

The embodiments described above may be implemented by any hardware, software or a combination of hardware and software having the above described functions. The software code, instructions and/or statements, either in its entirety or a part thereof, may be stored in a computer readable memory. Further, a computer data signal representing the software code, instructions and/or statements, which may be embedded in a carrier wave may be transmitted via a communication network. Such a computer readable memory and a computer data signal and/or its carrier are also within the scope of the present invention, as well as the hardware, software and the combination thereof.

The present invention has been described with regard to one or more embodiments. However, it will be apparent to persons skilled in the art that a number of variations and modifications can be made without departing from the scope of the invention as defined in the claims.

What is claimed is:

1. A method of processing one or more input signals including one or more physiological signals, comprising:
converting one or more input signals in a time-domain into one or more information signals in a frequency domain through an over-sampled analysis filterbank, the one or more input signals including one or more physiological signals;
implementing subband signal processing on the information signals in accordance with an application associated with the physiological signal, the subband signal processing step including extracting one or more features from the information signal;
synthesizing one or more subband signals output from the subband signal processing through an over-sampled synthesis filterbank to provide one or more time domain output signals;
combining the one or more features with the one or more time domain output signals, in the time-domain.

2. A method as claimed in claim 1, wherein the combining step combines the features, time-domain signals associating with the physiological signals, or combinations thereof.

3. A method as claimed in claim 1, comprising the step of:
implementing time-domain signal processing on the physiological signal that is provided to the over-sampled analysis filterbank as the input signal.

4. A method as claimed in claim 3, wherein the subband signal processing and the time-domain signal processing are interacted.

5. A method as claimed in claim 3, wherein the combining step combines the one or more features, the output from the time-domain processing, or combinations thereof.

6. A method as claimed in claim 1, comprising the step of:
obtaining one or more feedback signals through the combining step; and
providing the feedback signal to the over-sampled analysis filterbank as the input signal.

7. A method as claimed in claim 1, wherein the step of converting comprises:
converting the one or more input signals in the time-domain through one or more over-sampled, Weighted-Overlap-Add (WOLA) analysis filterbanks, and
the method comprising:
converting the (possibly processed) subband signals back to the time-domain using one or more over-sampled, WOLA synthesis filterbanks.

8. A method as claimed in claim 1, further comprising at least one of the following steps:
storing the subband signal,
transmitting the subband signal, and
receiving the subband signal.

9. A method as claimed in claim 8, wherein the subband processing step obtains, as its input, the stored signal or the received signal.

10. A method as claimed in claim 9, wherein the combining step obtains, as its input, the stored signal or the received signal.

11. A method as claimed in claim 1, further comprising as least one of the following steps:
storing the output of the time-domain processing step,
transmitting the output of the time-domain processing step, and
receiving the output of the time-domain processing step.

12. A method as claimed in claim 11, wherein the time-domain processing step obtains, as its input, the stored signal or the received signal.

13. A method as claimed in claim 11, wherein the combining step obtains, as its input, the stored signal or the received signal.

14. A method as claimed in claim 1, wherein the subband signal processing includes the step of:
implementing beamforming algorithm.

15. A method as claimed in claim 1, wherein the subband signal processing includes the step of:
implementing subband adaptive filtering on the information signals.

16. A method as claimed in claim 1, wherein the subband signal processing includes the step of:
implementing active noise cancellation.

17. A method as claimed in claim 1, wherein the subband signal processing includes the step of:
implementing autocorrelation estimation using one or more complex subband signals by IIR or FIR methods, for the purpose of heartbeat detection or other applications.

18. A method according to claim 1, comprising:
selectively providing a feedback signal output from the combiner or the physiological signal to the over-sampled analysis filterbank as the input signal.

19. A system for processing an input signal, comprising:
module for converting one or more input signals in a time-domain into one or more information signals in a frequency domain, the one or more input signals including one or more physiological signals;
module for implementing subband signal processing on the information signals in accordance with an application associated with the input signal, the subband signal processing module including a module for extracting one or more features from the information signal;
an over-sampled synthesis filterbank for synthesizing one or more subband signals output from the subband signal processing module to provide one or more time-domain signals;
a combiner for combining the one or more features with the one or more time domain output signals, in the time-domain.

20. A system as claimed in claim 19, wherein the combiner combines the features, time-domain signals associating with the physiological signals, or combinations thereof.

21. A system as claimed in claim 19, further comprising:
module for implementing time-domain signal processing on the physiological signal that is provided to the over-sampled analysis filterbank as the input signal.

22. A system as claimed in claim 21, wherein the subband signal processing module and the time-domain signal processing module interact.

23. A system as claimed in claim 21, wherein the combiner combines the one or more features, the output from the time-domain processing module, or combinations thereof.

24. A system as claimed in claim 19, comprising:
a switch for selectively providing a feedback signal output from the combiner or the physiological signal to the over-sampled analysis filterbank as the input signal.

25. A system as claimed in claim 19, wherein the combiner provides a feedback signal to the subband signal processing module.

26. A system as claimed in claim 19, wherein:
the over-sampled analysis filterbank includes an over-sampled, WOLA analysis filterbank.

27. A system as claimed in claim 19, further comprising module adapted for at least one of the following steps;
storing the subband signal,
transmitting the subband signal, and
receiving the subband signal.

28. A system as claimed in claim 27, wherein the subband processing module obtains, as its input, the stored signal or the received signal.

29. A system as claimed in claim 27, wherein the combiner obtains, as its input, the stored signal or the received signal.

30. A system as claimed in claim 19, further comprising modules adapted for at least one of the following steps;
storing the output of the time-domain processing module,
transmitting the output of the time-domain processing module, and
receiving the output of the time-domain processing module.

31. A system as claimed in claim 30, wherein the time-domain processing module obtains, as its input, the stored signal or the received signal.

32. A system as claimed in claim 31, wherein the combiner obtains, as its input, the stored signal or the received signal.

33. A system as claimed in claim 19, wherein the subband signal processing module implements beamforming algorithm.

34. A system as claimed in claim 19, wherein the subband signal processing module implements subband adaptive filtering on the information signals.

35. A system as claimed in claim 19, wherein the subband signal processing module implements active noise cancellation.

36. A stethoscope for processing a physiological sound signal, comprises:
an over-sampled filterbank for transforming an electrical signal associating with a physiological sound signal into a plurality of subband signals;
an adjustor for implementing subband gain adjustment to the subband signals from the over-sampled analysis filterbank;

a first processing module for decimating and encoding the subband signals output from the over-sampled analysis filterbank, during a record operation;

a second processing module for decoding and interpolating the decimated, encoded subband signals output from the first processing module, during a playback operation;

an over-sampled synthesis filterbank coupling to a main audio output channel and an auxiliary channel, for synthesizing an output from the adjustor in the main channel and synthesizing the output from the second processing module in the auxiliary channel; and a feedback path for feed-backing an output of the auxiliary channel to the over-sampled analysis filterbank in the playback operation.

37. A stethoscope as claimed in claim 36, wherein the programmable digital signal processor implements the method of claim 1.

* * * * *